US009820951B2

(12) United States Patent
Torres et al.

(10) Patent No.: US 9,820,951 B2
(45) Date of Patent: Nov. 21, 2017

(54) PULMONARY DISEASE TREATMENT AND DIAGNOSIS BASED ON ARHGEF1

(75) Inventors: Raul M. Torres, Denver, CO (US); John Hartney, Arvada, CO (US); Roberta Pelanda, Denver, CO (US)

(73) Assignees: NATIONAL JEWISH HEALTH, A NON-PROFIT ORGANIZATION, Denver, CO (US); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 75 days.

(21) Appl. No.: 13/979,410

(22) PCT Filed: Jan. 13, 2012

(86) PCT No.: PCT/US2012/021216
§ 371 (c)(1),
(2), (4) Date: Jul. 12, 2013

(87) PCT Pub. No.: WO2012/097232
PCT Pub. Date: Jul. 19, 2012

(65) Prior Publication Data
US 2013/0289121 A1 Oct. 31, 2013

Related U.S. Application Data

(60) Provisional application No. 61/433,109, filed on Jan. 14, 2011.

(51) Int. Cl.
| | | |
|---|---|---|
| *C12Q 1/68* | (2006.01) |
| *A61K 31/192* | (2006.01) |
| *G01N 33/577* | (2006.01) |
| *A61K 31/18* | (2006.01) |
| *A61K 31/403* | (2006.01) |
| *A61K 31/4178* | (2006.01) |

(52) U.S. Cl.
CPC ............ *A61K 31/192* (2013.01); *A61K 31/18* (2013.01); *A61K 31/403* (2013.01); *A61K 31/4178* (2013.01); *C12Q 1/6883* (2013.01); *G01N 33/577* (2013.01); *C12Q 2600/106* (2013.01); *C12Q 2600/136* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 6,673,908 B1 | 1/2004 | Stanton, Jr. | |
| 2006/0019272 A1* | 1/2006 | Geraci | ............... 435/6 |
| 2010/0004331 A1 | 1/2010 | Hutchinson et al. | |
| 2010/0056527 A1* | 3/2010 | Eatherton | ............ C07D 405/06 514/236.5 |

OTHER PUBLICATIONS

Hall S. (2006) Thromboxane A2 Receptor Antagonists. Medicinal Research Reviews, 11(5):503-579.*
Brown et al. (2007) Arhgef1 Is Required by T Cells for the Development of Airway Hyperreactivity and Inflammation. American Journal of Respiratory and Critical Care Medicine, 176:10-19.*
Lowrey et al. (2008) MMP-9 protein level does not reflect overall MMP activity in the airways of patients with COPD. Respiratory Medicine, 102:845-851.*
Belvisi et al. (2003) The role of matrix metalloproteinases (MMPs) in the pathophysiology of chronic obstructive pulmonary disease (COPD): a therapeutic role for inhibitors of MMPs? Inflammation Research, 52:95-100.*
Hegele. (2002) SNP Judgments and Freedom of Association. Arterioscler Thromb Vasc Biol, 22:1058-1061.*
Hartney et al. (2010) Arhgef1 Regulates alpha5-beta1 Integrin-Mediated Matrix Metalloproteinase Expression and Is Required for Homeostatic Lung Immunity. The American Journal of Pathology, 172(3):1157-1168.*
Glinsky et al. (2006) Integration of HapMap-Based SNP Pattern Analysis and Gene Expression Profiling Reveals Common SNP Profiles for Cancer Therapy Outcome Predictor Genes. Cell Cycle, 5(22):2613-2625.*
Nicolaou et al. (1979) Synthesis and biological properties of pinane-thromboxane A2, a selective inhibitor of coronary artery constriction, platelet aggregation, and thromboxane formation. PNAS, 76(6):2566-2570.*
Rolin et al. (2006) Prostanoids as pharmacological targets in COPD and asthma. European Journal of Pharmacology, 533:89-100.*
Barnes et al. (2005) COPD: current therapeutic interventions and future approaches. European Respiratory Journal, 25(6):1084-1106.*
Ishiura et al. (2003) Thromboxane antagonism and cough in chronic bronchitis. Annals of Medicine, 35:135-139.*
MedlinePlus ("Chronic Bronchitis" obtained from < https://medlineplus.gov/chronicbronchitis.html> on Oct. 27, 2016, 6 pages).*
Allan et al. (1994) Characterization of Human Peripheral Blood Monocyte Thromboxane A2 Receptors. The Journal of Pharmacology and Experimental Therapeutics, 270 (2):446-452.*
Hartney, et al., (2010) Arhgef1 Regulates α5β1 Integrin-Mediated Matrix Metalloproteinase Expression and Is Required for Homeostatic Lung Immunity, The American Journal of Pathology, vol. 176, No. 3, Issue 3, pp. 1157-1168.

(Continued)

*Primary Examiner* — Neil P Hammell
(74) *Attorney, Agent, or Firm* — William A. Ziehler; Shumaker, Loop & Kendrick LLP

(57) ABSTRACT

Treatment and diagnostic methods are provided for pulmonary disease, including chronic obstructive pulmonary disease, Arhgef1, a leukocyte signaling molecule, functions normally to suppress integrin-mediated MMP production by alveolar macrophages. MMP9 production by fibronectin-stimulated monocytes and macrophages depends on autocrine thromboxane receptor signaling and this signaling pathway is attenuated by Arhgef1. Expression of ARHGEF1 by human peripheral blood monocytes varies between individuals and inversely correlates with fibronectin-mediated MMP9 production. Arhgef1 levels can function as a predictor for a pulmonary disease candidate and a thromboxane receptor antagonist can treat a pulmonary disease condition resulting from low Arhgef1 levels.

5 Claims, 21 Drawing Sheets

(56) References Cited

OTHER PUBLICATIONS

Hartney, et al., (2006) Prostaglandin E2 Protects Lower Airways Against Bronchoconstriction, American Journal Physiol. Lung Cell Mol. Physiol 290, L105-L113.

* cited by examiner

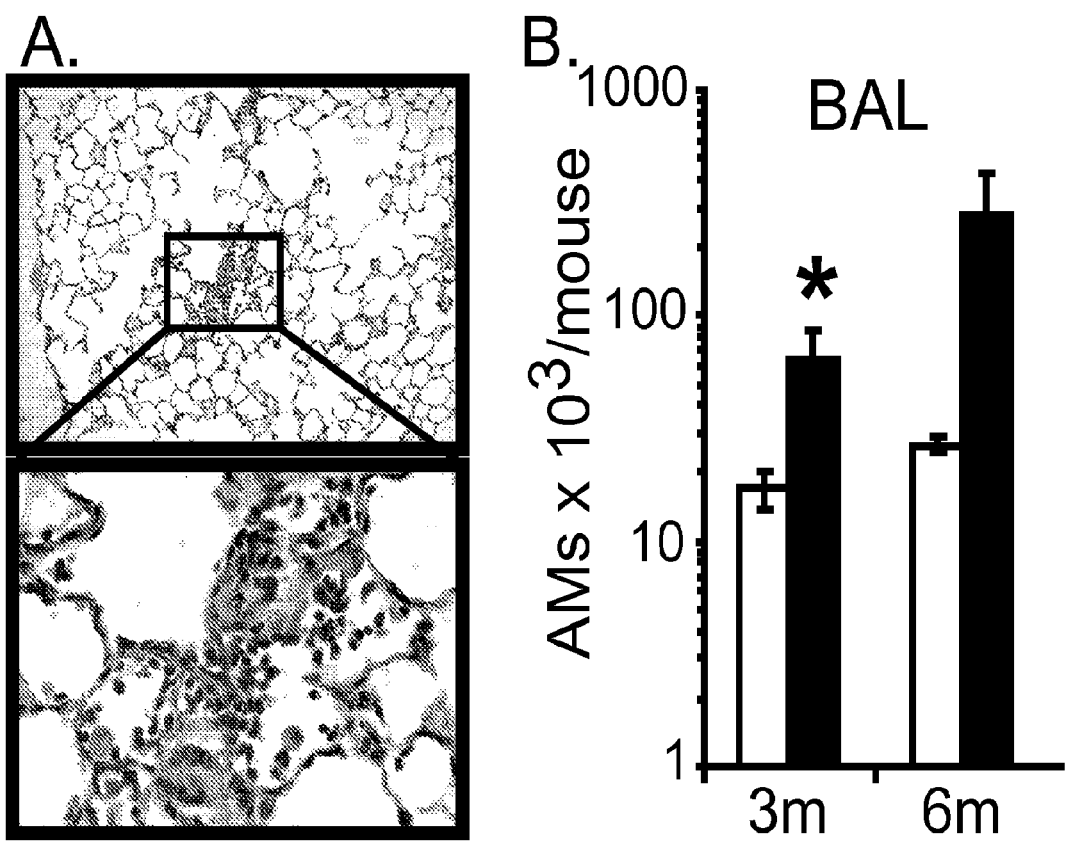
FIG. 1A-B

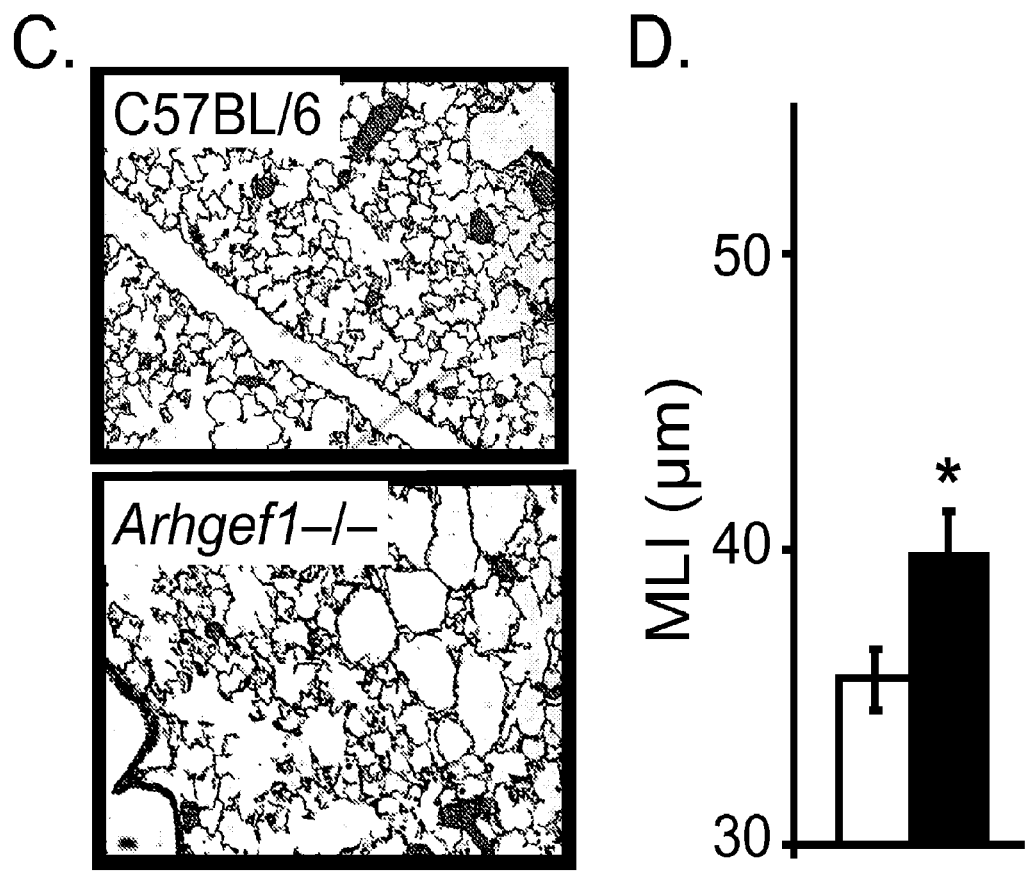
FIG. 1C-D

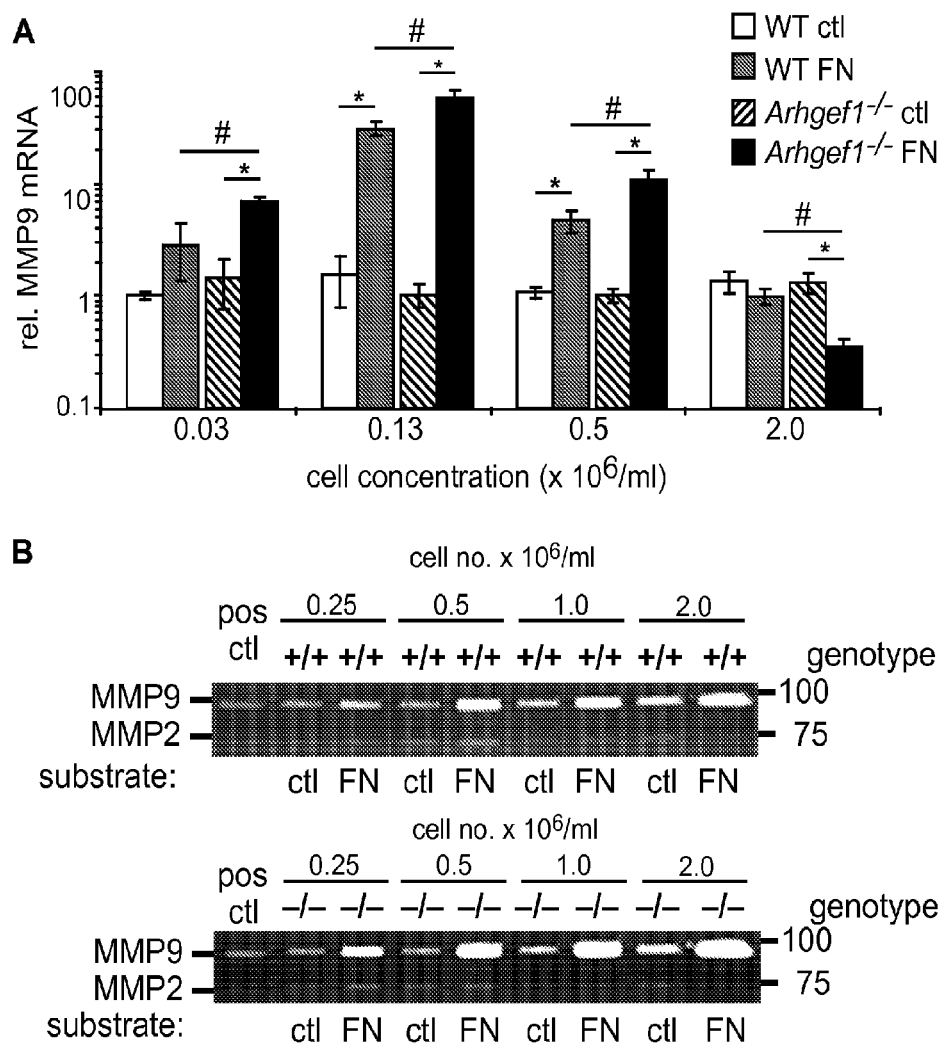
FIG. 10A-B

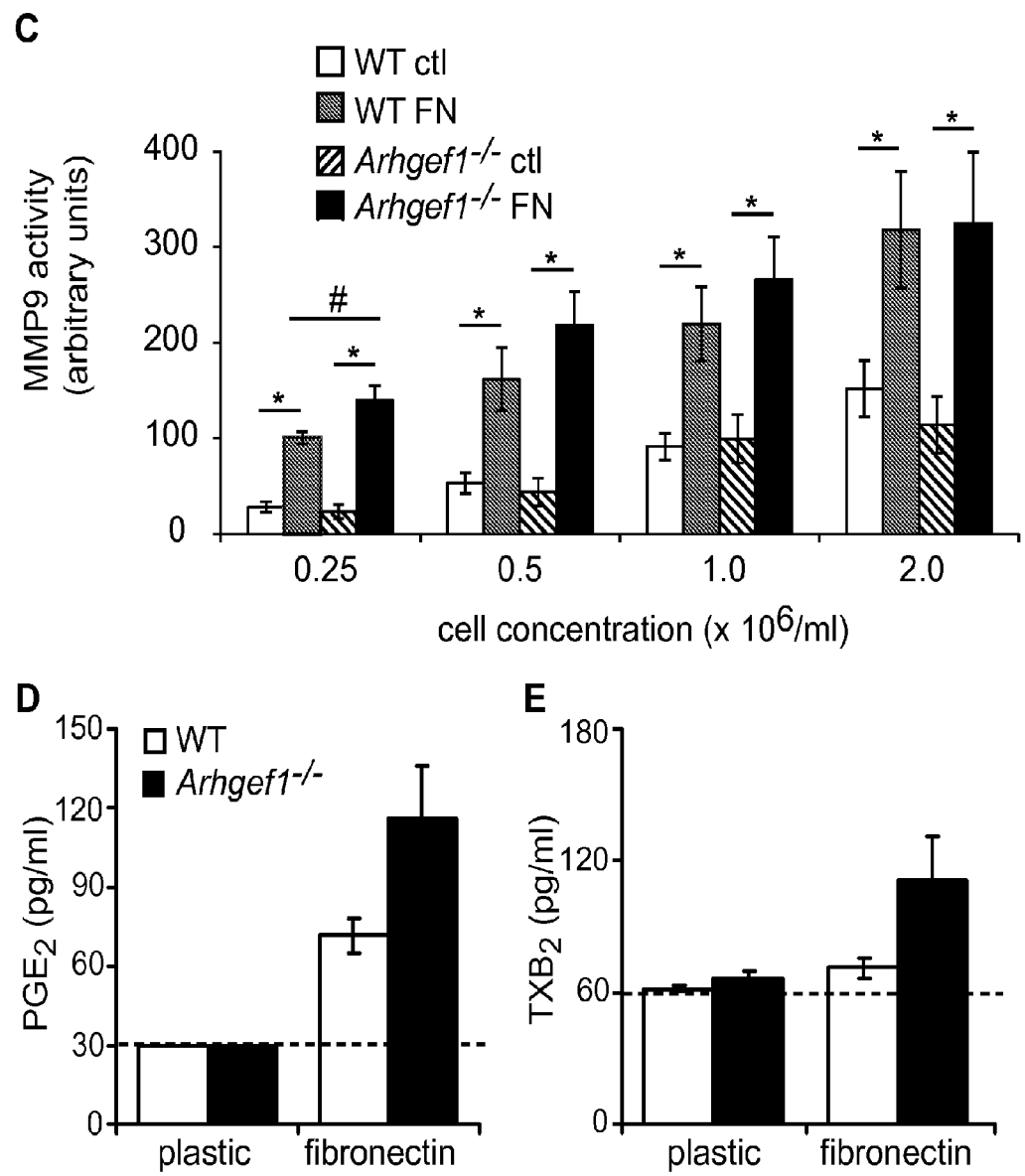
FIG. 10C-D

PULMONARY DISEASE TREATMENT AND DIAGNOSIS BASED ON ARHGEF1

CROSS-REFERENCE TO RELATED APPLICATIONS

This application claims the benefit of U.S. Provisional Application No. 61/433,109, filed on Jan. 14, 2011. The entire disclosure of the above application is incorporated herein by reference.

GOVERNMENT RIGHTS

This invention was made with U.S. government support under grant number AI1007045 awarded by the National Institutes of Health. The U.S. government has certain rights in the invention.

FIELD OF THE INVENTION

The present technology relates to treatments and diagnostics for pulmonary disease, including those associated with macrophage autocrine thromboxane receptor signaling of matrix metalloproteinase 9 and those using the level of Arhgef1 expression/activity in a subject as a prognosis or to diagnose or treat a subject for a pulmonary disease such as chronic obstructive pulmonary disease.

BACKGROUND OF THE INVENTION

This section provides background information related to the present disclosure which is not necessarily prior art.

Inflammation is a host response to infection important for pathogen elimination but that also leads to tissue injury that must be repaired. Accordingly, this response must be tightly regulated as aberrant, or excessive inflammation can also result in tissue injury caused by responding leukocytes. Moreover, prolonged pro-inflammatory stimulation or an inability to resolve acute inflammation can contribute to the pathogenesis of a number of diseases that include chronic obstructive pulmonary disease, asthma, cancer, atherosclerosis, and autoimmunity. With regards to chronic obstructive pulmonary disease, continual stimulation through repeated cigarette smoke exposure leads to chronic inflammation that is perpetuated even years after cigarette smoke exposure has terminated. Thus, defining the molecular pathways that lead to inflammation, and the identification of possible points of intervention in these pathways is warranted.

The acute inflammatory response to pathogens initiates with tissue injury and/or exposure of pathogen-derived ligands that engage toll-like receptors expressed on resident tissue macrophages. Macrophages are innate immune cells that reside in diverse tissues and provide sentinel responses against pathogens or noxious substances by the production of pro-inflammatory vasoactive lipids, cytokines, and chemokines. An immediate consequence of this tissue macrophage response is the recruitment of neutrophils that within hours release their granule contents at the site of infection in an attempt to eradicate or neutralize pathogens. However, this response can also lead to local tissue injury. Recruited macrophages, differentiated from newly arriving monocytes, clear remaining pathogens and short-lived apoptotic neutrophils via phagocytosis and begin tissue repair through the production of angiogenic factors and proteolytic tissue enzymes such as matrix metalloproteases (MMPs). Under normal circumstances, the acute inflammatory response to pathogen exposure is resolved within days.

In tissues, macrophages use integrins to adhere to integrin ligands found in extracellular matrix (ECM) proteins (e.g. collagen and fibronectin) or expressed on the cell surface of other cells (e.g. ICAM and VCAM). The adhesion of myeloid cell to ECM integrin ligands has repeatedly been shown to promote production of many pro-inflammatory mediators such as prostaglandins, inflammatory cytokines, chemokines, and multiple MMPs. Although the production of prostaglandins is known to be dependent on cyclooxygenase activity, the integrin signaling pathways macrophages use to produce other pro-inflammatory mediators are not well understood, although mitogen-activated protein kinases, Src family, and Pyk2 nonreceptor tyrosine kinases are implicated in integrin signaling. Work from our laboratory has found that macrophage adhesion to fibronectin via the $\alpha 5\beta 1$ integrin in vitro leads to MMP9 production and is normally inhibited by the Arhgef1 intracellular signaling molecule.

Arhgef1 (Lsc/p115RhoGEF) is an intracellular signaling molecule with expression predominantly restricted to hematopoietic cells. Arhgef1 has been biochemically and functionally characterized as both a regulator of G-protein signaling (RGS) and Rho guanine nucleotide exchange factor. RGS proteins act as GTPase-activating proteins for GTP-bound Ga subunits of heterotrimeric G-proteins. Arhgef1 specifically accelerates the inherent GTPase activity of $G\alpha_{12/13}$ subunits, thereby terminating signaling from GPCRs that associate with $G\alpha_{12/13}$-containing heterotrimeric O-proteins. Arhgef1 also contains a tandem Dbl and pleckstrin homology domain that functions as Rho guanine nucleotide exchange factor specific for RhoA. RhoA participates in a number of cell biological processes including regulating cytoskeletal organization, integrin adhesion, and integrin signaling. We have shown that in B-lymphocytes, Arhgef1 is required for resolving integrin adhesion, and analyses of Arhgef1-deficient mouse mutants have further demonstrated a requirement for Arhgef1 in leukocyte migration and adhesion, consistent with the reported role for Arhgef1 in fibroblast adhesion to fibronectin.

SUMMARY OF THE INVENTION

The present technology includes systems, processes, methods, articles of manufacture, and compositions that relate to pulmonary disease treatments and diagnostics. Thromboxane receptor signaling is required for fibronectin-induced matrix metalloproteinase 9 (MMP9) production by human and murine macrophages and that the signaling is attenuated by the Arhgef1 molecule. In particular, Arhgef1$^{-/-}$ macrophages exhibit exaggerated matrix metalloproteinase (MMP) 9 production when cultured on fibronectin. Thromboxane is produced by myeloid cells when cultured on fibronectin, and treatment with thromboxane receptor (TP) antagonist ablates MMP9 production. Accordingly, TP signaling is required for MMP9 production by myeloid cells cultured on fibronectin. TP antagonists can therefore be therapeutic for reducing myeloid MMP9 production in inflammatory diseases.

In some embodiments, a method for treating a pulmonary disease in a subject is provided that comprises administering a therapeutically effective amount of a thromboxane receptor antagonist to the subject. The pulmonary disease can include chronic obstructive pulmonary disease (COPD). The administering can include parenteral (e.g., inhalation) or enteral (e.g., oral) administration routes, including administration by inhalation of the thromboxane receptor antagonist by the subject. The thromboxane receptor antagonist can include a member selected from the group consisting of pinane thromboxane A2, L-655,240, L-670,596, Terutroban, PRT061103, Ifetroban, Ramatroban, Seratrodast, Z-335, Ridogrel, Terbogrel, ICI-185,282, ICI-192,605, and combinations thereof.

In other embodiments, a method for diagnosing a subject as a pulmonary disease candidate is provided that comprises determining leukocyte expression of Arhgef1 in the subject and identifying the subject as a pulmonary disease candidate when leukocyte expression of Arhgef1 in the subject is reduced compared to leukocyte expression of Arhgef1 in a healthy individual. The leukocyte can include an alveolar macrophage, a monocyte, a monocyte-derived macrophage, or a neutrophil. Determining leukocyte expression of Arhgef1 in the subject can include determining whether the subject is an Arhgef1+/− heterozygote. Determining leukocyte expression of Arhgef1 in the subject can also include single nucleotide polymorphism (SNP) genotyping to identify ARHGEF1 haplotypes predictive of ARHGEF1 expression, measuring ARHGEF1 expression by qPCR, or measuring ARHGEF1 expression by flow cytometric analysis.

Various embodiments provide a method for diagnosing a subject as a pulmonary disease candidate and treating the pulmonary disease candidate that include the diagnostic and treatment methods described herein.

Still further embodiments provide a method of selecting a candidate compound for treating a pulmonary disease in a subject. A leukocyte comprising a thromboxane receptor is exposed to a compound. Whether the compound inhibits the thromboxane receptor in the leukocyte is determined. The compound is selected as a candidate compound for treating the pulmonary disease when the compound inhibits the thromboxane receptor. The pulmonary disease can comprise chronic obstructive pulmonary disease (COPD) and the leukocyte can comprise an alveolar macrophage, a monocyte, a monocyte-derived macrophage, or a neutrophil. In some embodiments, determining if the compound inhibits the thromboxane receptor comprises measuring at least one of an expression of MMP9 and an activity of MMP9 in the leukocyte, wherein the compound inhibits the thromboxane receptor if the expression of MMP9 or the activity of MMP9 is reduced in the leukocyte.

Also provided is a method of treating a pulmonary disease in a subject comprising administering to the subject a therapeutically effective amount of a candidate compound selected according to one or more of the methods described herein.

Some aspects of the technology provide methods for determining a likelihood of effectiveness of a pulmonary disease treatment using a thromboxane inhibitor in a subject. As used herein, the term "thromboxane inhibitor" includes thromboxane receptor inhibitor, thromboxane synthase inhibitor, or any inhibitor that inhibits expression (e.g., siRNAs) or the activity of thromboxane synthase. Methods of the technology include determining the level of Arhgef1 in leukocytes, pulmonary cells, or a combination thereof of the subject or ARHGEF1 haplotype of the subject. In general, if the level of Arhgef1 of the subject is less than the level of Arhgef1 in a control group or if the subject is heterozygous (ARHGEF1+/−) or homozygous (ARHGEF1−/−), then it is an indication that the thromboxane inhibitor treatment is likely to be effective in treating the subject's pulmonary disease. In some embodiments, the pulmonary disease comprises chronic obstructive pulmonary disease.

Other aspects of the technology provide methods for determining the presence of or the likelihood of developing chronic obstructive pulmonary disease (COPD) in a test subject comprising determining the level of Arhgef1 expression in the test subject, and comparing the level of Arhgef1 expression in the test subject with a control Arhgef1 expression level to determine the presence of or the likelihood of developing chronic obstructive pulmonary disease.

In some embodiments, the control Arhgef1 expression level comprises the level of Arhgef1 expression in a subject without COPD, and wherein a significantly lower level of Arhgef1 expression level in the test subject compared to the control Arhgef1 expression level is an indication that the test subject has or is likely to develop COPD.

Yet in other embodiments, the control Arhgef1 expression level comprises the level of Arhgef1 expression in a subject with COPD, and wherein a statistically lower level of Arhgef1 expression level in the test subject compared to the control Arhgef1 expression level is an indication that the test subject has or is likely to develop COPD.

Still other aspects of the technology provide methods for determining whether to treat a subject suffering from COPD with a thromboxane inhibitor, the method comprising determining the level of Arhgef1 expression in the subject suffering from COPD, and comparing the level of Arhgef1 expression in the subject with a control Arhgef1 expression level to determine whether to treat the subject with a thromboxane inhibitor.

In some embodiments, the control Arhgef1 expression level comprises the level of Arhgef1 expression in a subject without COPD, and wherein a significantly lower level of Arhgef1 expression level in the subject suffering from COPD compared to the control Arhgef1 expression level is an indication that the subject suffering from COPD is likely to benefit from thromboxane inhibitor treatment.

In other embodiments, the control Arhgef1 expression level comprises the level of Arhgef1 expression in a subject with COPD, and wherein a statistically similar level of Arhgef1 expression level in the subject suffering from COPD compared to the control Arhgef1 expression level is an indication that the subject suffering from COPD is likely to benefit from thromboxane inhibitor treatment.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 10. Fibronectin induces macrophage to produce MMP9, $PGE_2$, and $TXB_2$. A, Mmp9 expression was measured by qPCR in peritoneal macrophages cultured on FN (10 μg/ml) or plastic (ctl) plated at the indicated cellular concentrations and cultured for 48 h. Mmp9 expression is shown on a log scale as fold induction over expression of wild type cells cultured on plastic (ctl) at each respective concentration. The number of experiments at each concentration (0.03, 0.13, 0.5, and $2.0 \times 10^6$ cells/ml) for wild type cells on plastic (open bars) are represented by n=3, 5, 10, and 3, respectively; wild type cells on fibronectin (gray bars) are represented by n=3, 12, 12, and 3; Arhgef1$^{-/-}$ cells on plastic (hatched bars) are represented by n=3, 6, 11, and 3; Arhgef1$^{-/-}$ cells on fibronectin (black bars) are represented by n=3, 12, 12, and 3. The data represent the means±S.E. B, representative zymogram of conditioned media from peritoneal macrophages cultured on either plastic (ctl) or FN at the indicated cellular concentrations from wild type (+/+) and Arhgef1$^{-/-}$ (−/−) samples. Molecular weight standards and respective enzymatic activities of MMP9 and MMP2 are shown. C, quantitation of MMP9 activity as determined by densitometric analyses of zymograms. MMP9 activity is shown in arbitrary units and represents n=7 for wild type cells on plastic (open bars) and on fibronectin (gray bars) at all cellular concentrations. For Arhgef1$^{-/-}$ samples, n=6 for cells on plastic (hatched bars) and on fibronectin (black bars) at all cellular concentrations. The data represent the means±S.E. D, $PGE_2$ was measured by ELISA in conditioned media from macrophages cultured for 48 h on either plastic or fibronectin. For wild type (open bars), n=4, and for Arhgef1$^{-/-}$ (black bars), n=6. The data represent the means±S.E. The dotted line indicates the limit of detection. E, $TXB_2$ was measured by ELISA in conditioned media from macrophages cultured for 48 h on either plastic or fibronectin. For wild type (open bars), n=4, and for Arhgef1$^{-/-}$ (black bars), n=6. The data represent the means±S.E. The dotted line indicates the limit of detection, *, p<0.05 Student's two-tailed t test comparing MMP9 expression/activity on fibronectin to respective cells on plastic. #, p<0.05 Student's two-tailed 1 test comparing wild type to Arhgef1$^{-/-}$ cells under identical conditions.

DETAILED DESCRIPTION OF EXEMPLARY EMBODIMENTS OF THE INVENTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Abbreviations used herein include: MMP, matrix metalloproteinase; GPCR, G-protein coupled receptor; S1P, sphingosine-1-phosphate; LPA, lysophosphatidic acid; $TXB_2$, thromboxane $B_2$; PTXA2 and $PTA_2$, pinane-thromboxane $A_2$; $PGE_2$, prostaglandin $E_2$; FN, fibronectin; RGS, regulator of G-protein signaling; ECM, extracellular matrix; qPCR, quantitative PCR; LN, laminin; I-CAM, intracellular adhesion molecule 1; and V-CAM, vascular cell adhesion molecule 1.

The present technology relates to innate lung immunity in health and chronic obstructive pulmonary disease (COPD). Leukocytes are present in the lungs of healthy individuals and are necessary for the innate and adaptive immune response against potentially harmful foreign antigens that are inhaled on a constant basis. For antigenic challenges not cleared through mechanical expulsion or bactericidal agents, initial immune protection is provided by innate immunity and orchestrated by alveolar macrophages (AMs). Pathogens not eliminated by the innate immune response are subsequently met with the humoral and cellular arms of the adaptive immune response. Under normal circumstances, eradication of the inflammatory stimulus leads to resolution of inflammation and repair of the lung tissue. However, in the face of chronic stimulation tissue damage often ensues and is true of COPD where chronic stimulation is provided not only by long-term cigarette smoking, but also occupational dust and chemical exposure as well as biomass cooking and heating.

Figure 1E:
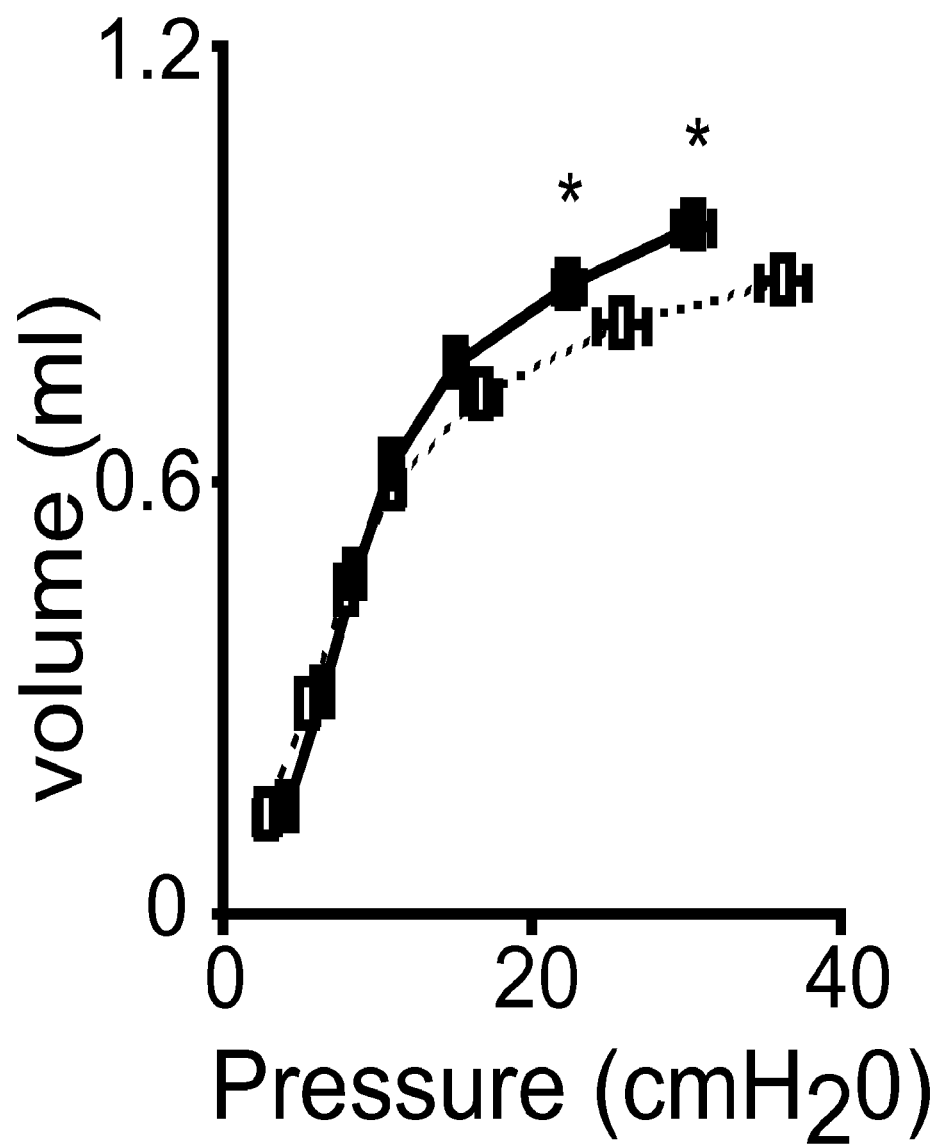
FIG. 1. Arhgef1−/− mice exhibit COPD like features. A. Histological sections of naïve (unchallenged) Arhgef1−/− lungs at 12 weeks reveal aggregations of leukocytes. B. Arhgef1−/− 3 and 6 month-old mice (filled; n=15, 5, respectively) harbor significantly more BAL macrophages compared to age-matched C57BL/6 mice (open; n—16, 3, respectively) and that increase in number with age. C. Arhgef1-deficient mice exhibit airspace enlargement relative to wild type. D. Alveolar wall loss as measured by mean linear intercept (MLI) of wild type (open; n=7) and Arhgef1-deficient (filled; n=9) lungs. E. Arhgef1-deficient mice (filled) display loss of elastic recoil in the lungs compared to C57BL/6 (open). Data are represented as mean±SE. *=p<0.05 two-tailed t-test.

COPD is a heterogeneous disease that is diagnosed clinically and organized into progressive stages delineated by degree of airflow obstruction. Two somewhat independent pathologies lead to COPD: loss of parenchymal lung tissue, or emphysema, which affects the elastic recoil of the lungs and a narrowing of the conducting airways and/or mucus hypersecretion, often referred to as obstructive bronchiolitis or small airways disease. The present inventors have shown in a mouse model that deficiency in leukocyte expression of Arhgef1, an intracellular signaling molecule, results in chronic inflammation in lung airspace and tissue, heightened matrix metalloproteinase (MMP) expression and activity, alveolar wall destruction (emphysema) and impaired lung function as indicated by reduced elastic recoil (FIG. 1). Interestingly, the present inventors have also found that leukocytes from individuals with COPD express significantly reduced levels of Arhgef1 protein compared with healthy individuals. Thus, the present data identify a novel association between Arhgef1, inflammation and parenchymal tissue damage providing insight into the molecular nature of COPD lung pathology.

Macrophages in health and in chronic obstructive pulmonary disease. Macrophages are considered sentinel in alerting lung innate and adaptive immune responses through their interaction with alveolar epithelial cells. In response to local inflammatory mediators produced by epithelial cells, AMs clear or neutralize potential harmful insults by migrating along the alveolar epithelium and facilitated by AM integrins interacting with respective integrin ligands produced by epithelial cells. Indeed, in response to inflammatory stimuli or injury, epithelial cells are induced to express integrin ligands such as the extracellular matrix component fibronectin. However, AMs have also been directly associated with lung tissue destruction in smokers and severity of COPD correlates with increased presence of these cells in addition to neutrophils and lymphocytes. It is believed that the subsequent response of AMs to these inflammatory mediators and integrin ligands expressed by these alveolar epithelial cells varies across individuals. Given that only a proportion of those chronically exposed to cigarette smoke develop emphysema, it is also believed that individuals whose macrophages exhibit exaggerated responses to these inflammatory mediators are predisposed for developing COPD.

An imbalance in protease/anti-protease levels leads to lung tissue destruction. The notion of an imbalance of proteases/anti-proteases in emphysema emerged with the identification over 40 years ago that individuals with genetic mutations in the SERPINA1 gene encoding α-1 antitrypsin are predisposed to the development of this disease. Since then an imbalance in the levels of several other proteases and anti-proteases in the pulmonary compartment have been associated with human lung pathology including MMP2, MMP9, MMP12 and TIMP-1 and genetic associations with COPD have been implicated for MMP9 and MMP12. Macrophages are known to express each of these MMPs and AMs from COPD patients express exaggerated levels of several of these proteases. Of note, MMP9 has repeatedly been shown to be elevated in AMs, lavage fluid, sputum, and serum from COPD individuals particularly implicating MMP9 in COPD pathophysiology. Further evidence supporting a protease imbalance as an etiological basis of lung tissue destruction is derived from mouse models whose macrophages either over-express MMP9 or are deficient in MMP 12 and that promote or are refractory to the development of airspace enlargement, respectively. Together, these data indicate that a protease/anti-protease imbalance promotes the development of lung pathophysiology. Of the pulmonary proteases, an increased presence of MMP9 is found in the lungs of emphysematous individuals where it has also been localized to the alveolar wall and site of tissue damage in emphysema and the present inventors have found that Arhgef1 acts to normally limit MMP9 production. Thus, a better understanding of how alveolar macrophages produce MMP9 and avenues to therapeutically interfere with the production of this MMP is warranted.

New signaling pathway for, and regulation of, MMP production by pulmonary leukocytes. An imbalance between protease and anti-protease activity is an established etiological basis for emphysema and MMPs are predominant pulmonary proteases that have also been implicated in lung pathology. Thus, identifying signaling pathways by which MMPs are generated within the lung is of fundamental importance. The present inventors have found a previously uncharacterized signaling pathway used by macrophages to generate MMP9 and that is negatively-regulated by Arhgef1. Because Arhgef1 has been shown to inhibit G-protein coupled receptor (GPCR) signaling, it is believed that within an inflammatory setting, signaling via a GPCR is a key component of MMP9 production leading to lung parenchymal tissue damage. Experiments by the present inventors show this GPCR is the thromboxane receptor expressed by pulmonary macrophages.

Establishing if an ARHGEF1 genetic signature is associated with Arhgef1 expression or MMP9 production. Experiments by the present inventors show that ARHGEF1 expression is genetically determined. In some embodiments, methods can be used as prognostic and/or diagnostic tests for COPD, a disease currently diagnosed by lung function testing and computer tomography. Additional objects, advantages, and novel features of the technology will become apparent to those skilled in the art upon examination of the following examples thereof, which are not intended to be limiting.

Example 1

This Example determines the macrophage signaling pathway regulated by Arhgef1 that leads to MMP production and whether protease production inversely correlates with Arhgef1 expression.

Figure 2:
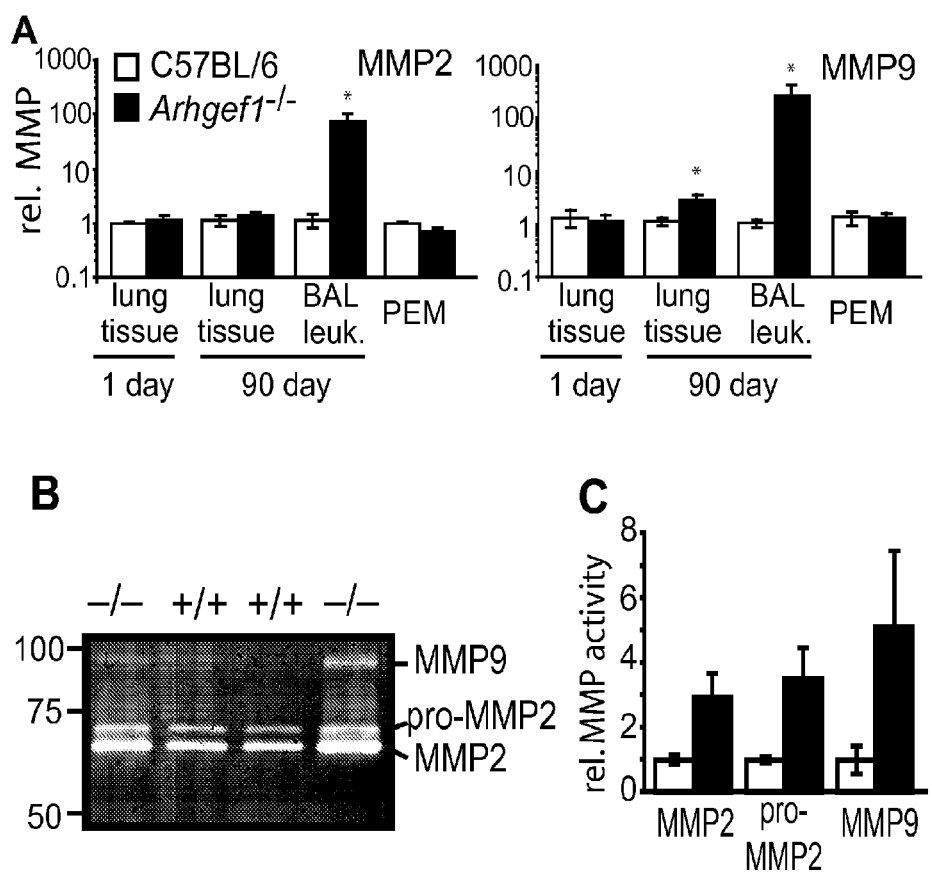
FIG. 2. Arhgef1−/− pulmonary leukocytes display increased MMP expression and activity. A) qPCR expression of Mmp2 and Mmp9 in day 1 whole lung, adult lavaged lung tissue and BAL leukocytes, and peritoneal elicited macrophages (PEM). Arhgef1−/− (filled), n=8; C57BL/6 (open), n=8. B) Gelatin zymography of wild type (+/+) and mutant (−/−) BAL supernatant. Molecular weight standards and respective enzymatic activity of MMPs are shown. C) Densitometric analysis of gelatin zymography with MMP activity shown as fold relative to control samples wild type (open bars) n=4 and Arhgef1−/− (solid bars) n=6 from two independent experiments.

Expression of Arhgef1 by pulmonary leukocytes is required for appropriate lung immune homeostasis and the present inventors have shown that Arhgef1 pulmonary leukocytes express significantly more MMP2, pro-MMP2, and MMP9 activity in bronchoalveolar lavage (BAL) compared to C57BL/6 controls (FIG. 2). Naïve (unchallenged) Arhgef1$^{-/-}$ mice also harbor more AMs (FIG. 1B) and both human and murine macrophages are known to produce MMPs, including MMP9, when cultured on integrin ligands. As both MMP9 and integrin ligand expression have been shown to be increased in COPD tissues and airspace, it is believed that Arhgef1 regulates macrophage integrin-mediated MMP9 production.

Figure 3:
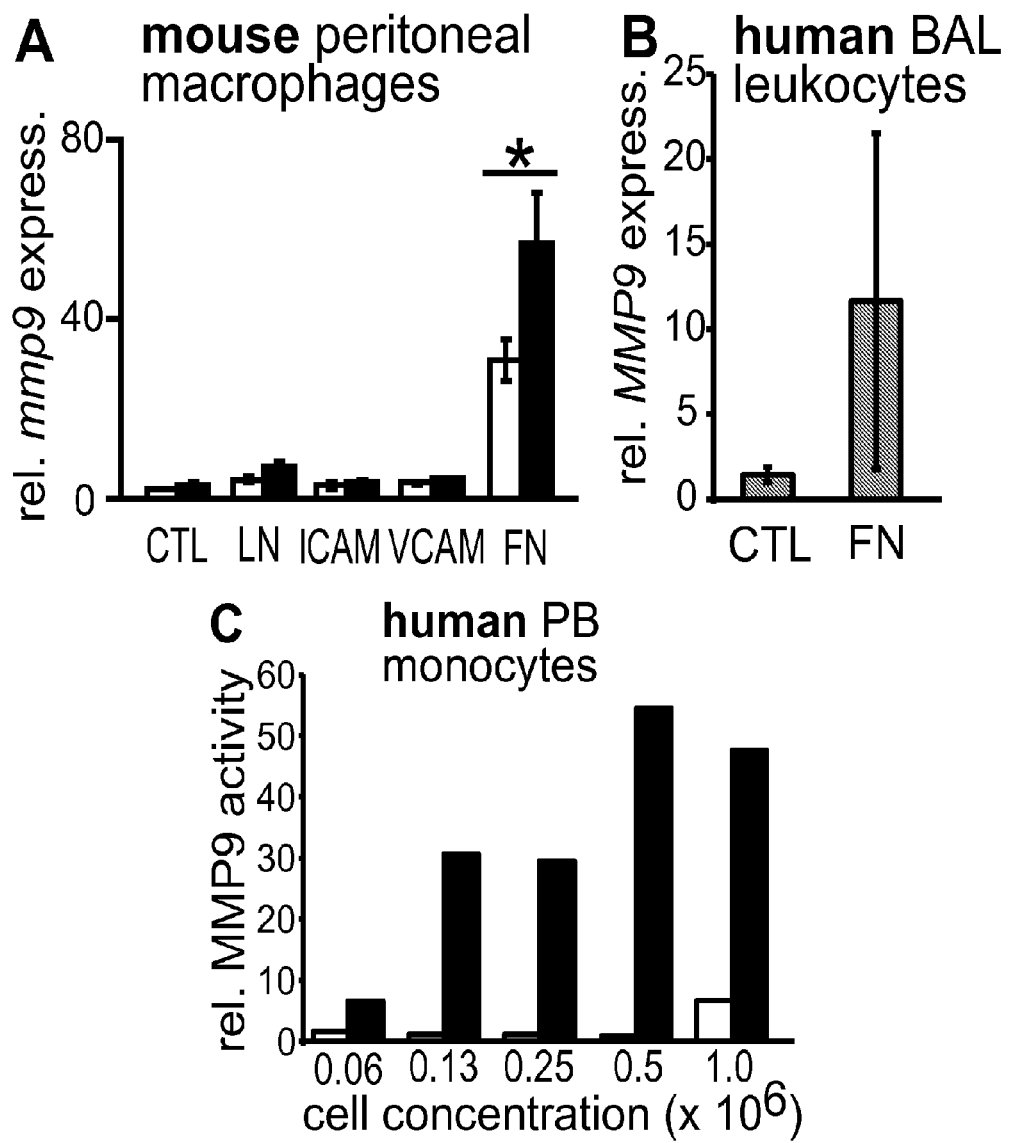
FIG. 3. A) B6 (open) mouse peritoneal macrophages express Mmp9 48 hours after culture on fibronectin and is exaggerated in the absence of Arhgef1 (filled). B) FN-mediated MMP9 expression by human BAL leukocytes (n=4) after 48 hours. C) Human peripheral blood monocyte MMP9 activity at different cell concentrations as measured by zymography after 48 hours on plastic (open) or fibronectin (filled).

Wild type and Arhgef1$^{-/-}$ peritoneal macrophages (that express minimal and equivalent amounts of MMP9 ex vivo, FIG. 2A) were cultured for 48 hours on cell-bound (ICAM-1 and VCAM-1) and ECM (laminin, and fibronectin) integrin ligands and the expression and activity of MMP9 measured by quantitative PCR (qPCR) and gelatin zymography, respectively (FIG. 3). These results confirmed the ability of fibronectin, and not other integrin ligands tested, to induce MMP9 expression and activity in wild type macrophages (FIG. 3). These findings also revealed that the α5β1 integrin was largely responsible for signaling fibronectin-induced MMP9 production and that in the absence of Arhgef1, macrophages expressed significantly more MMP9 compared to controls (FIG. 3). Together these data indicate Arhgef1 functions normally in macrophages to suppress integrin-mediated MMP production in vivo and in vitro. In addition, fibronectin also promoted considerable MMP9 expression in human BAL leukocytes (predominantly AMs; data not shown) from 4 individuals (FIG. 3B). While there was a relatively large variation in MMP9 expression by BAL leukocytes, the level of Arhgef1 expressed by the leukocytes from these individuals is believed to be inversely correlate with MMP9 expression. Moreover, fibronectin also induced MMP9 activity from human peripheral blood monocytes and over a wide range of cell concentrations (FIG. 3C). These data show this integrin-MMP9 signaling axis is operative not only in mouse but also human macrophages/monocytes thus facilitating comparison of MMP9 expression/activity with Arhgef1 expression from a given individual.

Fibronectin-mediated MMP9 expression by both mouse and human macrophages display a cell density dependence (FIG. 3C, FIG. 10A-C, FIG. 13A, and FIG. 15A-B) suggesting the possible contribution of a soluble trans-acting intermediate in integrin-mediated MMP production. Integrin signaling of MMP production has not only implicated MAPK activation but also has been shown to lead to the synthesis of prostaglandins that subsequently signals MMP9 production by macrophages.

Figure 4:
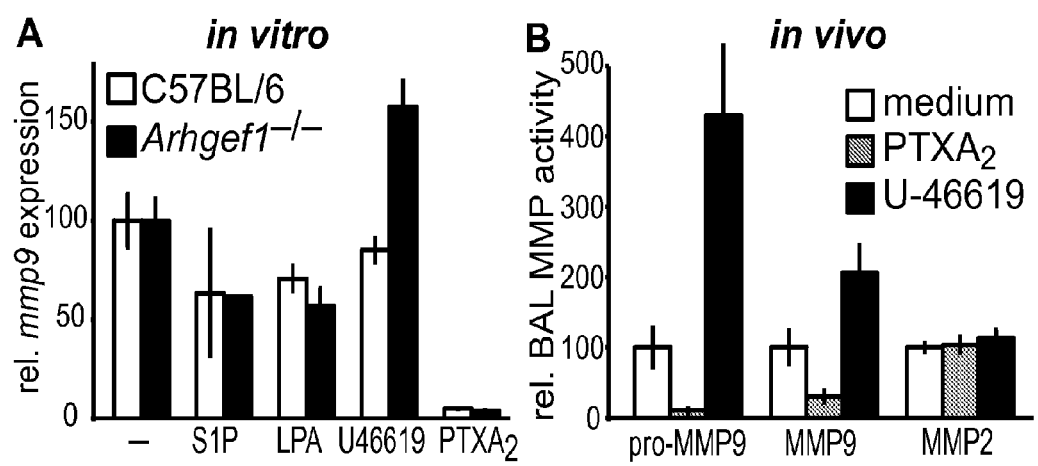
FIG. 4. TP signaling is required for MMP9 production in vitro and in vivo. A) Macrophage Mmp9 expression after culture on fibronectin for 24 hrs in media/vehicle (−), 40 nM S1P, 10 μM LPA, 10 nM U-46619 (TP agonist) or 6 μM PTXA2 (TP antagonist). Data represent normalized mean±SE. B) Arhgef1−/− mice (n=16) were exposed to aerosolized PBS (n=16), 220 μM PTXA2 (n=6) or 190 μM U-46619 (n=10) for 20 minutes and BAL harvested 1 day later and MMP activity measured.

Prostaglandins signal via cognate GPCRs and Arhgef1 regulation of GPCR signaling is restricted to a subset of GPCRs that associate with Gα12/13 heterotrimeric G-proteins. The family of prostanoid Gα12/13-associated GPCRs expressed by (pulmonary) macrophages is restricted but includes the thromboxane receptor (TP). Myeloid cells express TP and its ligand, thromboxane (TXA2), thus, experiments were performed to determine whether TP signaling altered fibronectin-mediated MMP9 production. As control, the lysophospholipids sphingosine-1-phosphate (S1P) and lysophosphatidic acid (LPA) whose Gα12/13-associated GPCRs are also expressed by macrophages and are regulated by Arhgef1 were also tested. Specifically, mouse peritoneal macrophages cultured on fibronectin were treated with S1P, LPA, a TP agonist (U-46619) or antagonist (pinane thromboxane A2; PTXA2) and MMP9 expression was measured. These results revealed that S1P and LPA act similarly on both wild type and mutant cells to modestly depress Mmp9 expression (FIG. 4A). In contrast, the U-46619 TP agonist considerably increased Mmp9 expression by Arhgef1-deficient macrophages but did not affect wild type cells (FIG. 4A). Antagonism of the TP by PTXA2 ablated Mmp9 expression by both wild type and Arhgef1-deficient cells further suggesting TP signaling was required for fibronectin-mediated MMP9 production by macrophages (FIG. 4A). Notably, these findings were also reflected in vivo as inhalation of PTXA2 considerably diminished MMP9 activity in the BAL of Arhgef1−/− mice 24 hours later while the U46619 TP agonist dramatically increased MMP9 activity (FIG. 4B). These effects appeared selective for MMP9 as no changes were observed in MMP2 activity with any treatment. These data show that TP signaling is required for integrin-mediated MMP9 production by macrophages in vitro and in vivo and Arhgef1 regulates this TP signaling.

Study of the macrophage signaling pathway regulated by Arhgef1. Without being bound by any theory, it is believed that integrin adhesion by alveolar macrophages promotes thromboxane receptor signaling that is responsible for MMP9 production and is negatively regulated by Arhgef1. The present inventors have studied the contribution of thromboxane receptor signaling to integrin-mediated MMP9 production by pulmonary macrophages. In addition, the present inventors are pharmacologically manipulating thromboxane receptor signaling in vivo and assessing whether lung pathology and function are ameliorated in Arhgef1$^{-/-}$ mice. The relationship between Arhgef1 expression and MMP9 production in macrophages from healthy individuals by either ARHGEF1 knock-down in high-expressing cells or increasing ARHGEF1 expression in low-expressing cells can be determined.

It was found that macrophage integrin signaling leads to MMP9 production in a pathway negatively-regulated by Arhgef1. The present inventors have discovered that this mechanism is dependent on thromboxane receptor (TP) signaling. Pharmacological and genetic in vitro and in vivo approaches are used to confirm the role of the TP in macrophage production of MMP9. This approach is used determine if the amount of MMP9 produced by macrophages is dependent on the level of Arhgef1 expressed. Manipulation of TP signaling in vivo and evaluating the consequence of this manipulation on MMP production and pathophysiology in wild type and Arhgef1-deficient mice is also used to study the mechanism. Enhancing or interfering with Arhgef1 activity in primary human myeloid cells in vitro is used to establish whether an inverse relationship exists between Arhgef1 levels and fibronectin mediated MMP9 production as indicated in findings by the present inventors.

Alveolar macrophages deficient in Arhgef1 expression produce elevated levels of MMPs in vivo and in vitro and Arhgef1$^{-/-}$ leukocytes promote pulmonary pathophysiology resembling emphysema. The present inventors have found that both integrin and TP signaling promote macrophage MMP9 production in vitro and both of these pathways are negatively-regulated by Arhgef1. These findings are directly relevant to human pathophysiology as elevated protease activity is a known etiological basis for emphysema and individuals with COPD display increased levels of pulmonary MMP9, integrin ligands, and systemic TXA2. The present inventors have investigated if macrophage integrin signaling promotes the generation of a TP ligand that then signals MMP9 production in a pathway regulated by Arhgef1. Defining whether an integrin-TP-MMP9 autocrine signaling pathway can lead to pulmonary pathology is important to understanding of how emphysema is established given the increased presence of both macrophages and MMP9 in the lungs of diseased individuals. In addition, establishing that aberrant thromboxane receptor signaling leads to lung tissue damage provides an attractive avenue of therapy for the treatment of COPD by pharmacological agents that target TP.

The following experimental methods and analyses were employed. Genetic analysis of the thromboxane receptor contribution to MMP9 production. In vitro analyses is used to determine the ability of peritoneal and alveolar macrophages isolated from Arhgef1$^{-/-}$, Tbxa2r$^{-/-}$ single and compound mutants to produce MMP9 as a result of fibronectin signaling. These experiments also allow assessment of additional ECM integrin ligands such as collagen and vitronectin to signal MMP production. A TP agonist (U-46619) and antagonist (pinane TXA2) are also included to control for specificity of these reagents expecting them to have no significant effect with Tbxa2r$^{-/-}$ macrophages opposed to Arhgef1$^{-/-}$ and wild type cells. These same mouse mutants are evaluated in vivo for pulmonary MMP production, lung tissue destruction and respiratory function. It is believed that the absence of TP prevents pulmonary pathology and restores lung function in Arhgef1$^{-/-}$ mice as a result of attenuating MMP production. It is also expected that pulmonary MMP9 expression in airspace and tissue is reduced in Tbxa2r$^{-/-}$ mice relative to controls. Arhgef1$^{-/-}$ and Tbxa2r$^{-/-}$ mouse mutants are available. Both strains are on a C57BL/6 genetic background.

In vivo TP manipulation. It is believed that Arhgef1−/−, Tbxa2r−/− compound mutants display improved pathology and/or lung function. Arhgef1−/− mutants are treated in vivo with TP antagonists (PTXA2 as in FIG. 4B in addition to seratrodast, a commercially available established and clinically relevant antagonist), to ameliorate pathophysiology. Specific measurements include enumeration of pulmonary leukocytes, MMP production, mean linear intercept, and evaluation of pulmonary function as measured by quasi-static pressure-volume loops using a Scireq flexiVent small animal ventilator. Wild type C57BL/6 mice are treated with a TP agonist (e.g. U-46619) and evaluated for the same parameters expecting to promote lung tissue destruction. In vivo treatments are optimized with respect to dose, kinetics and route of administration (i.t., i.n., i.p., inhalation via aerosolization). These experiments show if alveolar macrophage production of MMP9 in vivo is also dependent on TP signaling and provide information on whether inhibiting this signaling can improve lung function in animals that exhibit elevated MMP9 production. Of particular interest is in determining if TP antagonists ameliorate lung pathophysiology with the belief that manipulation of this receptor can be therapeutic for COPD.

Genetic manipulation of Arhgef1 expression in primary macrophages/monocytes. ARHGEF1 expression is altered in human macrophages/monocytes by Nucleofection technology, which was initially designed for primary cells with reported primary human macrophage and monocyte transfection efficiencies of up to 60% for both cell types. Others have successfully used this system to introduce expression vectors into primary human (and mouse) macrophages, including human alveolar macrophages. Arhgef1 level is increased in primary alveolar macrophages, monocytes or monocyte-derived macrophages (MDMs), by introducing an ARHGEF1-IRES-GFP retroviral expression vector or decreased by inserting an ARHGEF1-specific 70 shRNA within an appropriate IRES-GFP construct. In these experiments, transient expression of an ARHGEF1 cDNA or specific shRNA leads to GFP+ cells that either have elevated or decreased ARHGEF1 expression, respectively, and as confirmed by qPCR and an established intracellular flow cytometric analysis. Evaluation of MMP expression and activity in these genetically manipulated cells require that GFP+ cells be sorted prior to incubating on fibronectin. It is believed that Arhgef1 suppresses MMP9 production. This is demonstrated by relatively increased Arhgef1 levels promote reduced MMP9 expression and, conversely, that diminishing Arhgef1 levels promote increased MMP9. The addition of TP agonists and antagonists in cells that have manipulated Arhgef1 levels alter MMP9 production in a manner consistent with Arhgef1 negative-regulation of TP signaling.

Arhgef1 inhibits GPCR signaling via a specific (RGS) domain but also has a second defined function that activates RhoA via RhoGEF domain. The present inventors did not observe any significant role for Arhgef1-regulated RhoA activity in MMP production. The present inventors have generated and validated several Arhgef1 expression constructs that allow specific interrogation of both or either function. These constructs are used to evaluate these distinct Arhgef1 functions.

Human myeloid cells. Alveolar macrophages are obtained by lavage of healthy individuals. From BAL, typically around 5-10×10$^6$ cells are obtained of which >80% are typically alveolar macrophages. Further enrichment for macrophages can be achieved by culturing cells overnight on integrin ligands followed by vigorous washing before incubating an additional 24 hours. Peripheral blood is collected from subjects including those for which BAL cells are obtained and from ~8 ml typically yields at least 1-2×10$^6$ monocytes. MDMs are generated by culturing monocytes for 7 days in 10% human sera alone or in the presence of M-CSF and are empirically tested for MMP9 production. An aliquot of cells are evaluated for Arhgef1 expression by either qPCR and/or flow cytometric analysis.

MMP9 transcriptional and protein activity. MMP9 is measured directly in cultured human myeloid cells by qPCR as performed in FIG. 3B, FIG. 13A, and FIG. 15A and protease activity determined in supernatant by gelatin zymography. Due to the high level of transcriptional activity of macrophages on a per cell basis and the fact that secreted MMP9 accumulates with time in supernatant, the present inventors have determined that cell cultures can be scaled down to approximately 5×10$^4$ cells per condition. This allows assessment of a relatively large number of experimental variables in each patient sample. Also of interest is in determining if the level of MMP9 elicited varies across individuals and depending on Arhgef1 level.

Manipulation of Arhgef1 expression in myeloid cells results in an inverse correlation between Arhgef1 expression and myeloid cell production of MMP9 and that as in mice, Arhgef1 acts to suppress TP signaling. The in vivo and in vitro genetic and pharmacologic analyses of TP signaling of MMP9 production is used to confirm that fibronectin-mediated MMP9 production by macrophages is dependent on TP expression and is inhibited by Arhgef1. For example, double Arhgef1 and TP-deficient macrophages may produce decreased levels of MMP9 in vitro and in vivo double mutant mice may provide amelioration of lung pathophysiology. In some instances, TP-deficient pulmonary MMP9 may be reduced compared to wild type. Such experiments can also reveal whether fibronectin is the only ECM integrin ligand that promotes TP-mediated MMP9 production. It may also be determined that in vivo TP antagonism inhibits Arhgef1−/− lung MMP production, lessens tissue destruction, and improves lung function. These results may indicate that COPD individuals can be treated using seratrodast, a TP antagonist.

Alveolar macrophages are the relevant cell population whose aberrant production of MMPs is believed to promote lung pathology. Either monocytes or MDMs can also be used for these studies. As shown in FIG. 3, both human alveolar macrophages and monocytes respond on fibronectin to produce MMP9. One can compare the MMP9 response and ARHGEF1 expression between these two cell types from the same individual to establish their relationship. Myeloid cell lines which have much higher transfection efficiencies can also be used in the study. In vivo analyses reveal that Arhgef1−/− lung pathophysiology is independent of the TP and/or MMP9 production prompting a test to determine if additional MMPs are responsible (besides MMP2; FIG. 4B) or whether TP signaling suppresses the production of inhibitors of MMPs (e.g., TIMPS). When only modest reductions of MMP9 or lung tissue damage in Tbxa2r−/− single or compound mutants or pharmacologically manipulated mice is observed, the study necessitates determining whether MMP9, per se, or other proteases contribute to pathophysiology by analysis of MMP9-deficient mice bred onto Arhgef1−/− or Tbxa2r−/− genetic backgrounds.

Example 2

This Example establish whether integrin-mediated MMP production is exacerbated by oxidative stress, cigarette smoke or microbial infection, environmental stimuli relevant to emphysema.

Figure 5:
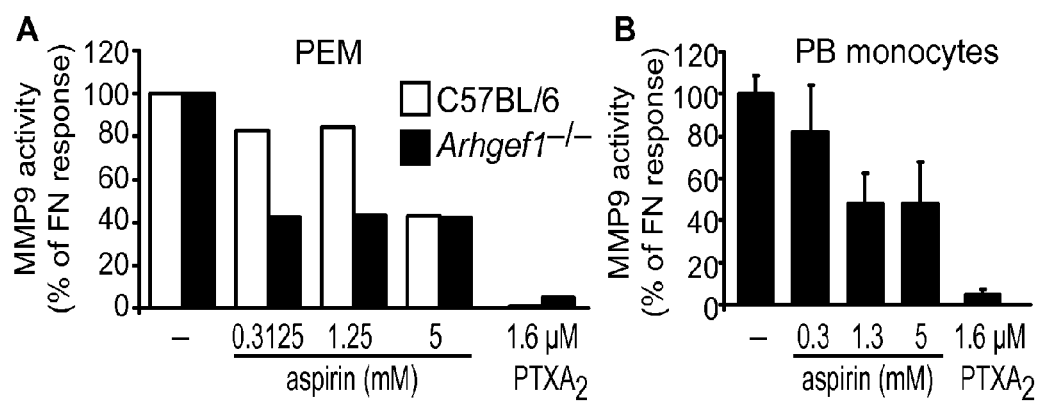
FIG. 5. TP-induced MMP9 production is only partially dependent on COX activity. A) PEMs were cultured on fibronectin for 24 hours with 5% FCS, washed then treated with different concentration of aspirin or 1.6 μM PTXA2 at for an additional 24 hours without FCS. MMP9 activity was determined by zymography from supernatants of wild type (open) or Arhgef1−/− (filled) macrophages. Activity was normalized to activity generated from cells cultured on fibronectin without treatment. B) MMP9 activity in conditioned media from peripheral blood monocytes cultured as described in panel A. Data represents mean±SE (n=3 independent donors).
Figure 6:
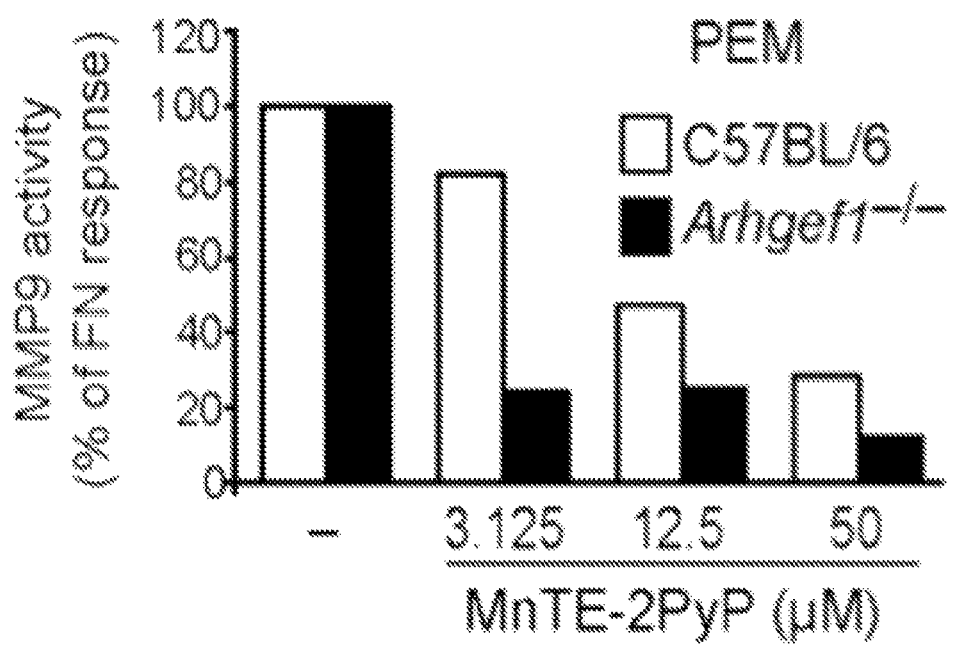
FIG. 6. The antioxidant mimetic MnTE-2PyP reduces MMP9 activity in macrophages. PEMs were cultured on fibronectin for 24 hours with 5% FCS, washed then treated with MnTE-2PyP at the indicated concentrations for an additional 24 hours without FCS. MMP9 activity was determined by zymography from supernatants of wild type (open) or Arhgef1−/− (filled) macrophages. Activity was normalized to activity generated from cells cultured on fibronectin without treatment.

Pulmonary oxidative stress is associated with COPD. The arachidonic acid metabolite, 8-iso-Prostaglandin F2α (8-iso-PGF2α isoprostane), is a common indicator of this oxidative environment and is elevated in the lungs of emphysematous individuals and produced by macrophages. Interestingly, 8-iso-PGF2α is also an alternate ligand for the thromboxane receptor but, in contrast to thromboxane, is generated from arachidonic acid by catalysis by reactive oxygen species and independent of cyclooxygenases. Thus, considering that macrophages produce reactive oxygen species during an inflammatory response and that smoking exacerbates an oxidative lung environment, an experiment is conducted to determine whether 8-iso-PGF2α contributed to TP signaling of MMP9 production. To determine if cyclooxygenase activity is required for MMP9 production, one of the experiments performed was adding the COX inhibitor, aspirin, to cultures of both mouse peritoneal macrophages and human monocytes cultured on fibronectin. As shown in FIG. 5, at the highest aspirin concentration (5 mM and >4-fold above the IC50 for COX1 and COX2, MMP9 activity was reduced only by ~40-50%. In contrast, the TP antagonist, PTXA2, virtually ablated fibronectin-mediated MMP9 activity by both mouse and human myeloid cells indicating that a COX-independent pathway made a substantial contribution to MMP9 production. Since free radical catalysis is required for production of 8-iso-PGF2α, the contribution of this isoprostane in MMP9 production is studied by adding the extracellular superoxide dismutase mimetic, MnTE-2PyP, to wild type and Arhgef1−/− macrophages cultured on fibronectin and measured MMP9 activity. These results (FIG. 6) revealed that the manganese porphyrin mimetic inhibited MMP9 activity produced by wild type macrophages by approximately 75% and by Arhgef1-deficient macrophages by approximately 90%. These data indicate that fibronectin-integrin signaling by macrophages in vitro employs a COX independent antioxidant-sensitive autocrine TP signaling pathway to elaborate MMP9. Experiments are also performed to determine if the 8-iso-PGF2α isoprostane is the autocrine mediator produced by macrophages that promotes MMP9 production.

Example 3

This Example establishes whether integrin-mediated MMP production is exacerbated by oxidative stress, cigarette smoke or microbial infection, environmental stimuli relevant to emphysema.

It is believed that environmental stimuli that promote emphysema act similarly to promote integrin-mediated TP-induced MMP9 production by pulmonary macrophages. Experiments are performed to determine if 8-iso-PGF2α isoprostane contributes to TP signaling of MMP9 production by macrophages. Experiments are also performed to determine whether primary human airway epithelial cells express integrin ligands that promote alveolar macrophage MMP9 production and to determine whether common microbial inflammatory stimuli induce MMP9 production via the TP signaling pathway. In addition, experiments are performed to determine whether cigarette smoke enhances MMP9 production in vivo and in vitro via the integrin-TP signaling pathway.

Experiments are performed to determine whether environmental stimuli that promote pulmonary inflammation, and associated with emphysema, also lead to macrophage MMP9 production through a common TP autocrine signaling pathway. In particular, experiments are performed to test how oxidative stress, endotoxin and cigarette smoke influence MMP9 production in vitro by wild type, Arhgef1−/−, and Tbxa2r−/− single and double mutant macrophages in the presence and absence of fibronectin or other integrin ligands. Initial efforts are used to establish if the 8-iso-PGF2α isoprostane, whose production is catalyzed by reactive oxygen species (ROS), contributes to fibronectin-mediated MMP9 production by macrophages. The contribution of endogenous and exogenous ROS towards macrophage MMP9 production is also explored. As a surrogate for microbial infection effects of endotoxin and other toll-like receptor ligands on MMP9 expression/activity by murine macrophages cultured on fibronectin and human macrophages co-cultured on primary airway epithelial cells are evaluated. In addition, how cigarette smoke impacts MMP production via this pathway both in vitro by human macrophage/primary airway epithelial cell co-culture and in vivo by whole body exposure of wild type and mutant mice is also evaluated. These experiments show whether this novel integrin-TP-MMP9 signaling pathway is specifically or generally exploited by environmental inflammatory stimuli that promote lung pathology and provides mechanistic insight into how the oxidative lung environment of chronic smokers leads to lung tissue damage.

Chronic inflammation is associated with emphysema and manifests with lung parenchymal tissue damage resulting from elevated protease activity. Of the various pulmonary proteases, the MMP9 protease is most often found increased in the lungs of COPD individuals and the present inventors have identified a novel autocrine TP signaling pathway used by pulmonary macrophages to produce MMP9. MMP9 is also normally inhibited by Arhgef1 Using human alveolar macrophages co-cultured with primary alveolar epithelial cells, experiments are performed to determine if this integrin-TP-MMP9 pathway operates in a physiologically relevant in vitro setting and how inflammatory stimuli influence this pathway. Furthermore, mouse mutants are used to genetically test in vitro and in vivo whether inflammation induced by oxidative imbalance, microbial infection or cigarette smoke similarly use the TP-MMP9 signaling axis or if this pathway is restricted to certain environmental stimuli. In particular, it is noted that elevated MMP expression and pathophysiology in naïve Arhgef1−/− mice is limited to the pulmonary compartment despite the presence of Arhgef1−/− macrophages in other organs, e.g., liver and spleen (data not shown). It is believed that ROS production by activated macrophages coupled with the elevated oxidative pulmonary environment leads to 8-iso-PGF2α and accounts for this discordance in tissue pathology. Finding that environmental inflammatory stimuli exacerbate macrophage MMP9 production via a TP autocrine signaling pathway provides an attractive therapeutic avenue for diseased individuals through TP antagonism.

The following experimental methods and analysis were employed. Oxidative imbalance in promoting integrin-mediated MMP9 production. Peritoneal and alveolar macrophages isolated from Arhgef1−/−, Tbxa2r−/− single and compound mutants are plated on fibronectin or plastic (or other ECM integrin ligands, if relevant) and MMP9 expression and activity measured after addition of the SOD mimetic, MnTE-2PyP, at various concentrations. ROS production by macrophages and suppression by the mimetic are assessed by fluorescence after loading cells with 10 μM of the ROS indicator, MitoSOX™ Red (Invitrogen). Integrin-mediated macrophage production of 8-iso-PGF2α is measured in the supernatant of parallel cultures using a commercially available (Cayman Chemicals) ELISA-based assay. These data indicate whether endogenous ROS, normally produced by macrophages during inflammation, are important for generating a TP ligand, and specifically 8-iso-PGF2α, that signals MMP9 production. The 8-iso-PGF2α isoprostane (commercially available) is also added to MnTE-2PyP-treated and control cultures to measure its ability to promote MMP9 production via a TP-specific signaling pathway and using the U-46619 TP agonist as a positive control. ROS in vitro is generated by adding xanthine and xanthine oxidase (100 μM and 0.01 U/ml, respectively) to macrophage cultures and again MMP9 production is measured. These experiments show whether an oxidative imbalance that is often associated with COPD promoted MMP9 signaling via an integrin-TP autocrine signaling pathway and whether the 8-iso-PGF2α isoprostane is the TP ligand that promotes this signaling.

Based on these in vitro findings, the MnTE-2PyP SOD mimetic is delivered to Arhgef1−/− mice (i.v., i.t., or inhalation) over various lengths of time after which respiratory function, lung tissue damage and MMP production is measured. It is expected that 8-iso-PGF2α levels diminish MMP9 production and also ameliorated pathophysiology.

LPS and additional TLR ligand promotion of macrophage MMP9 production. TLR signaling has been reported to promote MMP production by various cell types including MMP9 by macrophages. LPS (TLR4) and agonists for TLR2/6 (PAM3Cys), 3 (polyI:C), and 9 (CpG DNA) are added to macrophage cultures established from Arhgef1−/−, Tbxa2r−/− single and double mutants to assess whether microbial inflammatory stimuli exploit an integrin-TP-MMP9 autocrine signaling pathway. Based on the in vitro data indicating that these TLR agonists modulate macrophage MMP9 production, in vivo studies are performed to determine whether airway challenge of the same mouse mutants with these agonists similarly alter MMP9 production and pulmonary pathophysiology. If MMP9 is induced under these conditions, whether an integrin-mediated TP autocrine signaling pathway is operational is evaluated by the use of blocking integrin antibodies and TP pharmacological antagonists and agonists.

The ability of human alveolar macrophages cultured on normal human bronchial epithelial (NHBE) cells to produce MMP9 in the absence and presence of the same TLR agonists is also assessed. The culture of differentiated primary NHBE cells under an air-liquid interface is also studied. Briefly, $1\times10^5$ brushed bronchial epithelial cells are seeded onto 60 mm collagen-coated tissue culture dishes and incubated at 37° C. with 5% $CO_2$. At 80% confluence, cells are transferred onto collagen-coated transwell inserts ($4\times10^4$ cells/insert) in 12-well plates. After reaching confluence under the submerged condition, cells are shifted to an air-liquid interface, and alveolar macrophages seeded onto the apical side in minimal media and treated with or without TLR agonists. After 1-2 days, apical supernatant are harvested and tested for MMP9 activity. Control cultures contain only NHBE cells or alveolar macrophages. The concentration of macrophages cultured on airway epithelial cells and in which volume of medium is determined empirically using monocyte-derived macrophages. These experiments reveal if relevant primary epithelial cells express integrin ligands capable of inducing MMP9 production and whether protease production is exaggerated by low Arhgef1 expression.

Cigarette smoke exposure in vitro. In these experiments, macrophage-NHBE co-cultures are exposed to whole cigarette smoke (WCS) using a system that generates physiological relevant nicotine levels at the apical surface of cultured cells (12.5±0.4 ng/ml, data not shown). When the data shows that MMP9 is induced under these conditions, a test is conducted to determine if an integrin-mediated, TP autocrine signaling pathway is operational by the use of blocking integrin antibodies and TP pharmacological antagonists and agonists. These experiments show whether MMP 9 production by macrophages cultured with epithelial cells is exaggerated by cigarette smoke and whether an integrin-TP signaling axis is used for this production.

Cigarette smoke exposure in vivo. Single and compound mutants and wild type mice are exposed to CS over 1, 3 and 6 month periods using a TE-10 smoking system (Teague Enterprises, Davis, Calif.) for 6 hours/day, 5 days/week as whole body exposures. Control animals are exposed to filtered room air in separate TE-10 chambers. After CS exposure, the following are assessed: lung leukocyte numbers, respirator), mechanics, pulmonary MMP expression and activity, and lung tissue damage. Alveolar macrophages are isolated and evaluated for fibronectin-mediated MMP9 production and Arhgef1 levels (excluding Arhgef1−/− cells). These experiments also include treating CS-exposed wild type and Arhgef1−/− mice in vivo with the TP antagonist or SOD mimetic to determine whether oxidative stress is required for production of a TP ligand (presumably, 8-iso-PGF2α) that signals MMP9 production and leads to tissue damage. Together, these experiments provide information on whether CS inflammatory damage also proceeds via an integrin-TP signaling pathway that is regulated by Arhgef1.

These experiments reveal whether the identified integrin-TP-MMP9 macrophage signaling pathway is also used by common pulmonary inflammatory stimuli associated with emphysema. Specifically, it is expected that endogenous ROS production by macrophages leads to production of 8-iso-PGF2α that then acts on the TP to signal MMP9 production. This is an important finding that not only provides an example of how ROS indirectly alters macrophage signaling but also would provide mechanistic insight into why the oxidative lung environment is unique in exacerbated MMP9 production. It is expected that in vitro and in vivo cigarette smoke experiments provide information on whether this oxidative-promoting inflammatory stimulus promotes MMP9 production (and pathophysiology) by this same pathway.

With regards to pathogen associated TLR ligands that promote MMP production, these findings provide information on whether the integrin-TP-MMP9 signaling pathway is similarly used in response to microbial infections. Since certain bacterial and viral infections acutely exacerbate COPD, these findings also provide insight into mechanisms by which these exacerbations occur. Furthermore, co-culture of alveolar macrophages with primary NHBE cells provides physiological relevant evidence on this integrin-initiated and TP-mediated signaling pathway of MMP9 production in humans and that this pathway is employed by inflammatory stimuli by possibly promoting integrin ligand (fibronectin) expression or the independent generation of a TP ligand.

It is possible that the 8-isoprostane is not generated upon integrin signaling or cigarette smoke exposure or does not act on the TP to promote MMP9 production. However, given the ability of an antioxidant to inhibit MMP9 production (FIG. 6), this would suggest that oxidative stress nevertheless induces MMP9 and possibly via the oxidation of cysteine residues in signaling proteins. TLR stimulation has been shown to promote MMP production and this signaling may not signal via the TP or, if TP-dependent, may not rely on integrin signaling. Regardless, these results provide insight into the mechanisms by which bacterial and viral infections exacerbate COPD. Monocyte-derived macrophages or a macrophage cell line can also be used in these studies.

Example 4

This Example determines if an ARHGEF1 haplotype associates with monocyte Arhgef1 protein expression and/or in vitro MMP9 production.

Figure 7:
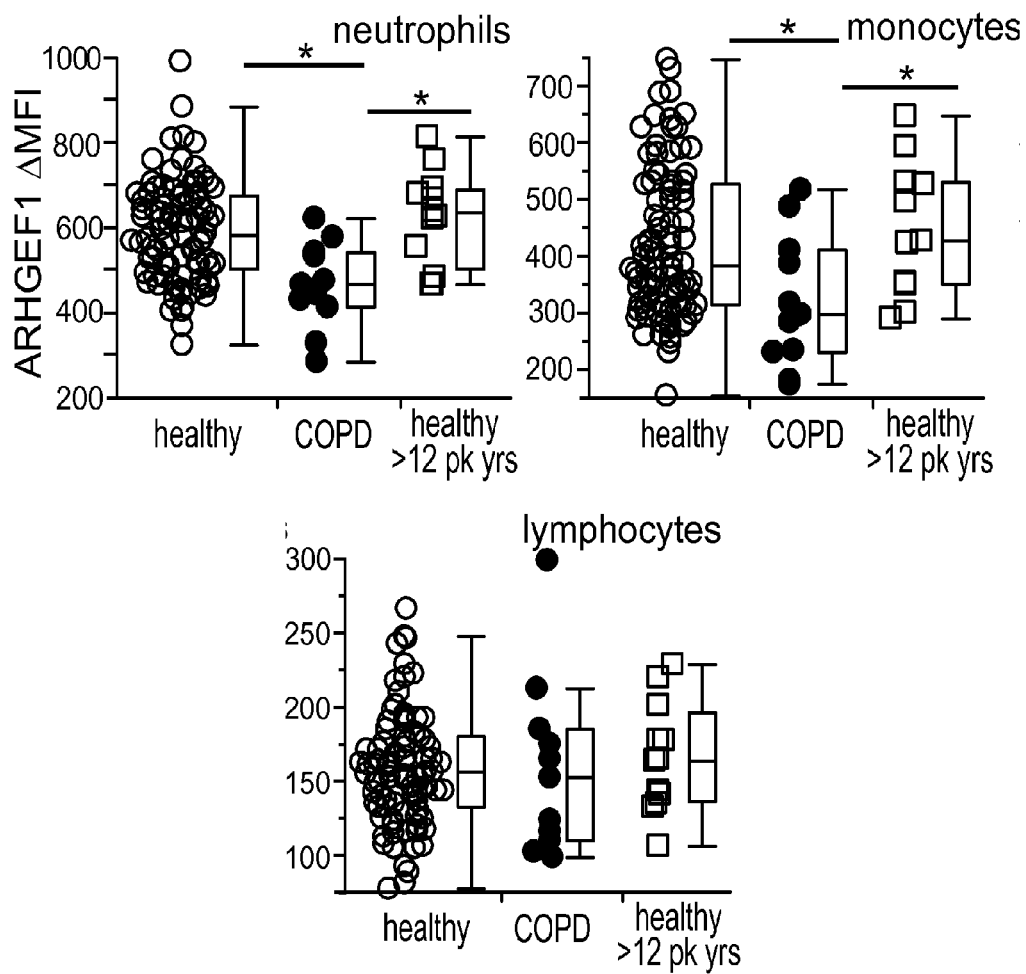
FIG. 7. Box whisker plots of Arhgef1 protein expression as determined by flow cytometric analysis for peripheral blood neutrophils, monocytes and lymphocytes. Individual and cohort average and range of Arhgef1 expression are shown for healthy individuals (open circles n=91) and COPD individuals (filled circles, n=11) and individuals within the healthy cohort that have >12 pack years of smoking history (open squares). *=p<0.005 Student's two tailed T-test comparing either healthy or healthy with >12 pack years of smoking to COPD individuals.

Mouse leukocytes that lack Arhgef1 expression promote pulmonary features reminiscent of emphysema. Intracellular flow cytometric analysis was used to measure Arhgef1 protein expression in PBLs collected from 102 healthy and COPD individuals. Monocytes, neutrophils and lymphocytes were distinguished by physical cell size (forward and side light scatter) and the CD45 and CD14 surface antigens. Arhgef1 expression in each individual was measured as the mean fluorescent intensity (MFI) obtained with a FITC-coupled anti-Arhgef1 monoclonal antibody (mAb) and subtracted from the MFI of an isotype control mAb to determine the relative Arhgef1 expression, or ΔMFI. These results revealed that Arhgef1 protein expression differed between individuals over an approximate 4-fold range with neutrophils expressing the highest levels, monocytes expressing intermediate levels and lymphocytes expressing the lowest levels (FIG. 7). Identification of individuals with COPD revealed Arhgef1 expression by their monocytes and neutrophils was significantly reduced relative to the same cell types in healthy individuals (FIG. 7). In contrast, both healthy and COPD lymphocyte populations expressed equivalent levels of Arhgef1. Reduced Arhgef1 expression by COPD leukocytes did not result from cigarette smoking as the same leukocyte populations from healthy individuals with >12 pack years of smoking history expressed similar Arhgef1 levels compared to all healthy individuals combined and significantly more than COPD individuals (FIG. 7). Thus, these data show that diminished leukocyte Arhgef1 protein expression appears to be associated with COPD. The consequence of variable Arhgef1 expression on MMP9 production is determined in some of the experiments. To address whether modest reductions in Arhgef1 are biologically relevant, Arhgef1 heterozygous (Arhgef1+/−), homozygous and wild type animals are compared. Arhgef1+/− BAL leukocytes expressed ~30% wild type levels of Arhgef1 and significantly more than Arhgef1−/− cells as measured by qPCR (FIG. 8A).

Figure 8:
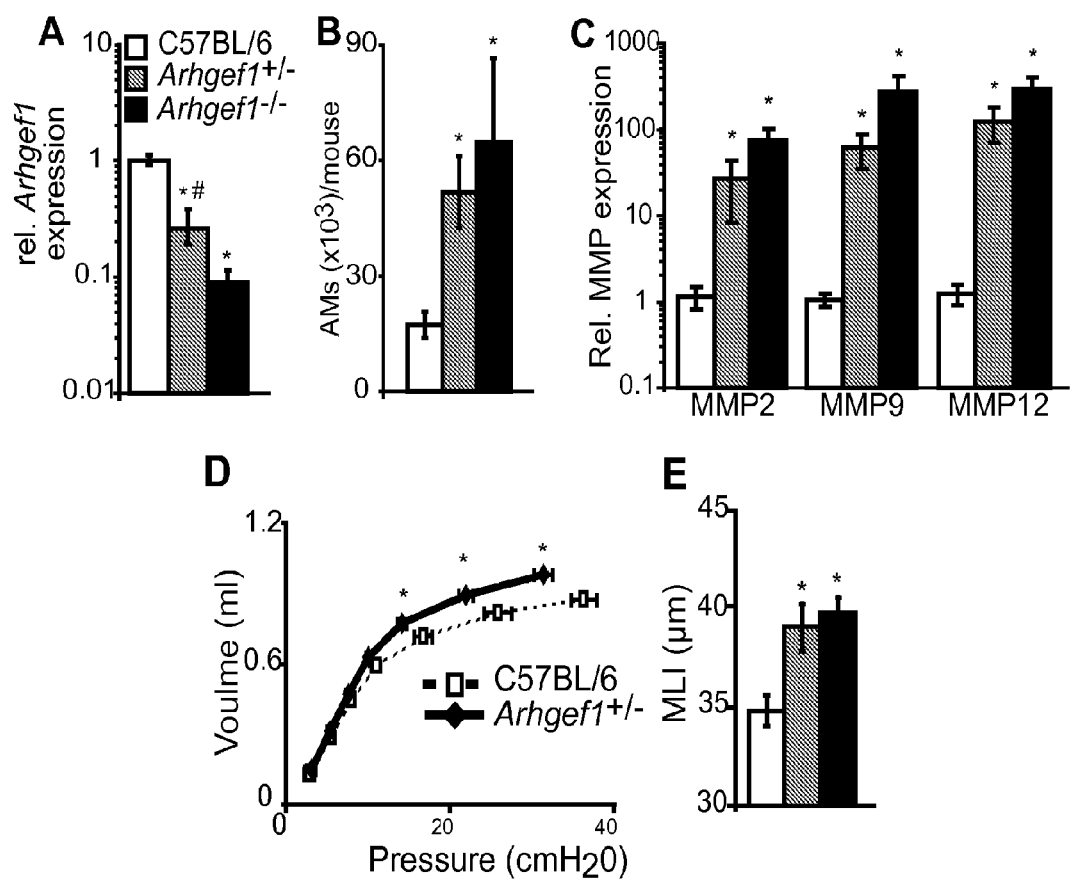
FIG. 8. Reduced Arhgef1 expression results in pulmonary pathology in the mouse. A) Arhgef1 expression in wild type (open bars; n=5), Arhgef1+/− heterozygous (gray bars; n=5) and Arhgef1−/− homozygous (black bars; n=6) samples as determined by qPCR. B) Number of alveolar macrophages recovered from BAL of 3 month old mice comparing wild type (n=15), Arhgef1+/− (n=7) and Arhgef1−/− (n=16) samples. C) MMP expression in BAL cells recovered from wild type (n=5), Arhgef1−/− (n=6) and Arhgef1+/− (n=5) mice. D) Lung mechanics on 3 month old wild type (n=8) and Arhgef1+/− (n=8) mice. E) Mean linear intercept of 3 month old mice comparing wild type (n=6), Arhgef1−/− (n=9) and Arhgef1+/− (n=7) mice. *=p<0.05 Student's two tailed t-test compared to wild type samples. #=p<0.05 Students two tailed T-test compared to Arhgef1−/− samples.
Figure 9:
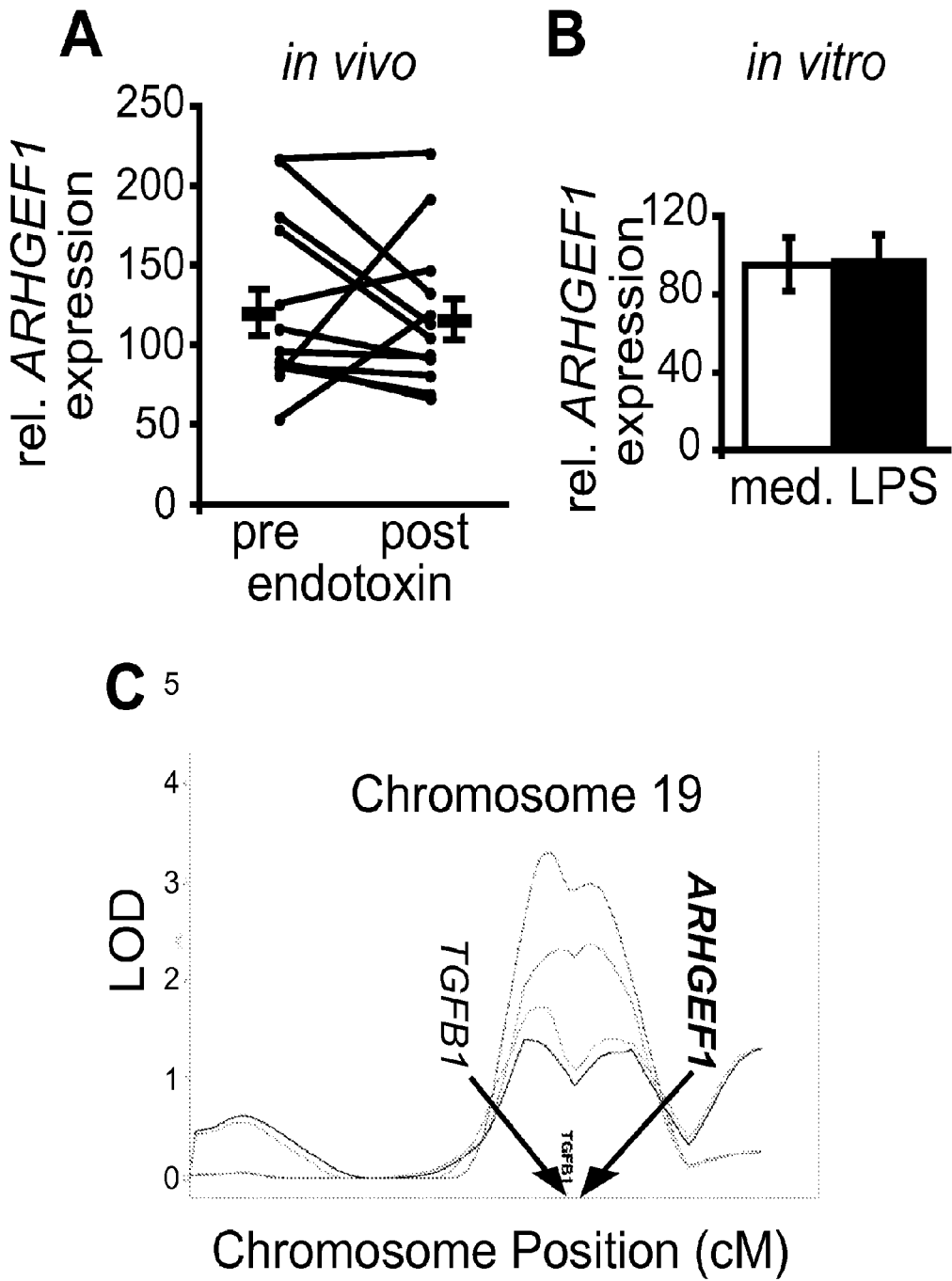
FIG. 9. Human neutrophil ARHGEF1 expression and chromosomal location. A) ARHGEF1 expression as measured by microarray analysis of peripheral blood neutrophils isolated from 14 subjects before and 16 hours after airway challenge with endotoxin. Connected points represent a given individual ARHGEF1 expression level before and after in vivo endotoxin exposure. Mean±SEM for pre- and post-exposure groups are indicated by bar. B) Mean ARHGEF1 expression in peripheral blood neutrophils isolated from 5 subjects and cultured for 1 hour with either media (open bar) or 100 ng/ml of LPS (filled bar). Data represents mean±SE. C) Genomic location of ARHGEF1 relative TGFB1 and LOD score of this locus for linkage to COPD phenotypes (adapted from Celedon et al., Hum Mol Genet, 2004, 13:1649).

Significantly, Arhgef1+/− mice also had increased numbers of BAL macrophages that expressed elevated levels of Mmp2, 9, and 12 compared to controls but less than Arhgef1-deficient cells (FIGS. 8B and C). Furthermore, Arhgef1+/− heterozygous mice also displayed significantly increased lung elasticity and MLI compared to wild type animals (FIGS. 8D and E). These data indicate that even a moderate decrease in Arhgef1 expression leads to pulmonary pathology and impaired lung function. Experiments were conducted to determine whether environmental or inflammatory stimuli altered Arhgef1 expression by exposing the airways of wild type mice to cigarette smoke (CS) or LPS. One month after daily smoke exposure or 1-2 days after LPS i.t. challenge, alveolar macrophage Arhgef1 expression was measured by qPCR and flow cytometry and found to be equivalent to that measured in naïve alveolar macrophages (data not shown). Similar results were also obtained with purified peripheral blood neutrophils (FIG. 9A) isolated from 14 healthy subjects before and 16 hours after endotoxin airway challenge. Neutrophils isolated from a subset of these individuals (preendotoxin exposure) and cultured in vitro for 1 hr±endotoxin followed by microarray analysis again showed comparable ARHGEF1 expression between non-stimulated and stimulated neutrophils (FIG. 9B) whereas a 200-fold increase in IL1A, a 93.5-fold increase in TNF and 9-fold increase in ICAM-1 expression was observed (data not shown). Together these data show that ARHGEF1 expression by human or murine leukocytes is resistant to change with either in vivo or in vitro endotoxin exposure and suggests expression may be genetically determined. In this regard, it is of interest that the genomic location of ARHGEF1 (19q13.2) maps precisely to a region previously associated with COPD related phenotypes in linkage analysis studies (FIG. 9C). While TGF-b1 has been considered the candidate gene within this region responsible for the pathogenesis of COPD, it is noted that ARHGEF1 is located within 0.53 Mb of TGF-b1 and, based on the present inventors' data, may also contribute to COPD pathophysiology.

It is believed that ARHGEF1 expression is genetically determined. Experiments are conducted to determine whether an ARHGEF1 haplotype associates with the level of Arhgef1 protein expressed by leukocytes. Experiments are also conducted to determine whether an ARHGEF1 haplotype associates with the level of monocyte integrin-mediated MMP9 production.

Experiments are performed to genotype ARHGEF1 tagging SNPs, which represent haplotypes, in a cohort of 100 healthy individuals to determine whether an ARHGEF1 haplotype associates with either the level of Arhgef1 protein monocytes express and/or MMP9 they produce in supernatant after culture on fibronectin. The level of Arhgef1 expression by monocytes from 102 individuals, including 11 individuals with COPD, has already been measured and genomic DNA is available from this same cohort to establish ARHGEF1 haplotypes providing further power to haplotype association analysis for Arhgef1 expression.

The level of ARHGEF1 protein and mRNA expression by leukocytes from healthy individuals varies over 4-fold (FIGS. 7, 9A, and 16), yet alteration in Arhgef1 expression in individuals or murine leukocyte has not been observed in in vivo or in vitro stimulation. These data indicate that ARHGEF1 expression is genetically determined and, coupled with the genetic association of the ARHGEF1 locus with COPD, prompted the present inventors to search for ARHGEF1 haplotypes that associate with either level of Arhgef1 and/or MMP9 production by monocytes. Selection of SNPs that serve to identify haplotypes (tagged-SNPs) is accomplished using the Tagger algorithm with criteria being a minor allele frequency >5% and with a pairwise $r2 \geq 0.80$ taken as indicative of redundancy. Experiments are designed to identify tag SNPs that are analyzed for haplotype association with these experimental parameters (Arhgef1 expression and MMP9 production) using standard software.

Haplotype-tagged SNP identification. ARHGEF1 is located on chromosome 19q13.2, spans 24.3 kilobases and harbors 29 exons. Haplotype-tagging single nucleotide polymorphisms (SNPs), which represent a set of individual SNPs, have been identified at the ARHGEF1 locus by the HapMap (www.hapmap.org) and Broad Institute Tagger server (www.broadinstitute.org/mpg/tagger/server.html). These tag SNPs are rs1428922 (minor allele frequency (MAF)=43%; located 7.5 kb 3' of ARHGEF1 ATG start site), rs882520 (MAF=8.3%; located within CD79A-ARHGEF1 intergenic region), rs3810153 (MAF=11%; located within CD79A-ARHGEF1 intergenic region) and rs891167 (MAF=8%; located within the first ARHGEF1 intron).

Measurement of monocytes ARHGEF1 expression and MMP9 production. Peripheral blood is collected from 100 healthy individuals and monocytes assessed for Arhgef1 protein by flow cytometric analysis (FIG. 7) and MMP9 activity (FIGS. 3C, 5B, 15B, 15C, 15F, 15G, and 16). From 8 ml of peripheral blood, typically $1-2 \times 10^6$ monocytes are recovered. As monocyte-derived MMP9 accumulates with time in supernatant, it was empirically determined that it is possible to measure MMP activity in supernatant from approximately $5 \times 10^4$ cells per well. Thus, even with triplicate wells and plastic control, this experiment can measure MMP9 production and Arhgef1 expression from a single individual.

ARHGEF1 SNP genotyping. SNP analysis is performed on genomic DNA from the monocyte-depleted PBLs (neutrophils and lymphocytes) using the Illumina Golden Gate Genotyping assay, which is a flexible, pre-optimized assay that uses a discriminatory DNA polymerase and ligase to interrogate up to 384 SNP loci simultaneously. The protocol is performed using the automated LIMS and AutoLoader. Association of tag SNPs and their haplotypes with both Arhgef1 expression and MMP9 production (and Hardy-Weinberg equilibrium) is evaluated with PLINK software (pngu.mgh.harvard.edu/Purcell/plink/).

It is believed that this experiment can identify ARHGEF1 haplotypes that are predictive of monocyte Arhgef1 expression, fibronectin-mediated MMP9 production or both. These data also provide evidence that the same ARHGEF1 haplotypes may be prognostic/diagnostic for COPD. These tag SNP(s) are evaluated in the COPD gene study (www.copdgene.org) in which cohort of individuals is characterized extensively for pulmonary function.

As the HapMap database is constantly updated, it is possible that additional tag SNPs that were not initially included can be identified. In some instances, ARHGEF1 protein expression may not show absolute correlation with ARHGEF1 expression. In fact, Arhgef1 has reported to undergo alternative-splicing in mouse splenocytes. However, this possibility was explored by qPCR using monocyte RNA isolated from several individuals and with primers that span introns 3', central, and 5' (reported site of alternative-splicing) of ARHGEF1. These results showed relatively similar amplification from all three regions (data not shown) indicating that alternative-splicing, if present, is not significant. It is further possible that qPCR measured ARHGEF1 expression can be correlated with flow cytometric analysis of ARHGEF1 expression.

The present technology further relates to MMP9 production by fibronectin-stimulated monocytes and macrophages, which is dependent on autocrine thromboxane receptor signaling, where under normal conditions this signaling pathway is attenuated by Arhgef1. The expression of ARHGEF1 by human peripheral blood monocytes is shown to vary between individuals and inversely correlates with fibronectin-mediated MMP9 production. Treatment and diagnostic methods are therefore possible.

During an inflammatory response, resident and newly recruited tissue macrophages adhere to extracellular matrix and cell-bound integrin ligands. This interaction induces the expression of pro-inflammatory mediators that include matrix metalloproteinases (MMPs). Arhgef1 is an intracellular signaling molecule expressed by myeloid cells that normally attenuates murine macrophage MMP production in vivo and in vitro after cell culture on the extracellular matrix protein, fibronectin. The present technology characterizes the fibronectin-induced Arhgef1-regulated signaling pathway in both human and murine myeloid cells. Our results show that MMP9 production by fibronectin-stimulated monocytes and macrophages depends on autocrine thromboxane receptor signaling and that under normal conditions, this signaling pathway is attenuated by Arhgef1. Finally, we show that the expression of ARHGEF1 by human peripheral blood monocytes varies between individuals and inversely correlates with fibronectin-mediated MMP9 production.

Arhgef1-deficient mice spontaneously develop pulmonary pathology, including a loss of alveolar structure that is accompanied by an increased presence of pulmonary macrophages and exaggerated production of MMP2, MMP9, and MMP12 by Arhgef1$^{-/-}$ alveolar macrophages. Exaggerated MMP9 production by Arhgef1$^{-/-}$ macrophages was further found to be recapitulated in vitro when cells are cultured on fibronectin and largely dependent on the α5β1 integrin. We have further investigated the macrophage signaling pathway regulated by Arhgef1 that leads to MMP9 production upon integrin-fibronectin interaction. We find that fibronectin induction of MMP9 by murine macrophages, as well as human alveolar macrophages and peripheral blood monocytes, is dependent on autocrine thromboxane receptor signaling, and this Gα$_{12/13}$-associated GPCR signaling is normally inhibited by Arhgef1. We further show that the expression of ARHGEF1 by human monocytes varies among individuals and is inversely correlated to in vitro fibronectin-mediated MMP9 production by these cells.

The following experimental procedures were employed.

Murine Macrophage Isolation

Peritoneal elicited macrophages were obtained by peritoneal lavage with 5 ml of ice-cold Hanks' balanced salt solution with 5 mmol/liter EDTA from mice 5 days after intraperitoneal injection of 1 nil of sterile thioglycollate as described by Hartney, J. M., Brown, J., Chu, H. W., Chang, L. Y., Pelanda, R., and Tones, R. M. (2010) Am. J. Pathol 176, 1157-1168. Resident peritoneal macrophages were obtained in the same manner in the absence of thioglycollate treatment. The cells were counted using a Z2 particle count and size analyzer (Beckman Coulter, Fullerton, Calif.) as described by Hartney, J. M., Brown, J., Chu, H. W., Chang, L. Y., Pelanda, R., and Torres, R. M. (2010) Am. J. Pathol 176, 1157-1168. Macrophages were resuspended in DMEM with 5% heat-inactivated fetal calf serum and plated at the indicated cellular concentrations.

Macrophage/Monocyte Culture Conditions—

Tissue-culture 96-well plates (Costar high binding catalogue number 3590) were coated with 10 μg/ml of murine fibronectin (Molecular Innovations, Nori, Minn.; catalogue number MFBN) or human fibronectin (Molecular Innovations; catalogue number HFBN) in DPBS without Ca$^{2+}$ or Mg$^{2+}$ (Mediatech, Inc., Manassas, Va.) for 2 h at room temperature. The cells at the indicated concentrations were added to each well in a 100-μl volume. The plates were centrifuged at 40×g for 1 min and then incubated for 24 h at 37° C. with 10% CO$_2$. Next, the wells were washed with PBS to remove nonadherent cells, and 100 μl of fresh DMEM without fetal calf serum was added to each well. In some experiments, the cells were treated with at this point with either sphingosine 1-phosphate, lysophosphatidic acid (Avanti Polar Lipids, Alabama), U-46619, L-655,240, pinane-thromboxane A$_2$ (PTA$_2$), or aspirin (Cayman Chemical Company, Ann Arbor, Mich.) after resuspension as per manufacturer recommendations. The plates were then incubated for an additional 24 h at 37° C. with 10% CO$_2$. Next, conditioned medium was removed and stored at −80° C. for subsequent analysis. PGE$_2$ and TXB$_2$ were measured in conditioned medium by ELISA according to the manufacturer's instructions (ElisaTech, Aurora, Colo.). The cells were treated with TRIzol (Invitrogen) for RNA purification as described by Hartney, J. M., Coggins, K. G., Tilley, S. L., Jania, L. A., Lovgren, A. K., Audoly, L. P., and Koller, B. H. (2006) Am. J. Physiol. Lung Cell Mol. Physiol. 290, L105-L113.

Human Alveolar Macrophages

Human alveolar macrophage were isolated from the bronchoalveolar lavage of healthy volunteers using protocols approved by the National Jewish Health Human Subjects Institutional Review Board. Six individuals (two males and four females) between the ages of 52 and 67 years of age participated in the study. The lavage cells were enumerated as described above for murine macrophages. The cells were then resuspended in DMEM with 5% FCS and plated at the indicated cellular concentrations in 96-well plates. Human cells were cultured as described for murine macrophages.

Human Peripheral Blood Monocytes

Peripheral blood monocytes were isolated from whole blood of healthy volunteers using protocols approved by the National Jewish Health Human Subjects Institutional Review Board. Ten individuals (five males and five females) between the ages of 45 and 68 years of age participated in the study. Whole blood was obtained by venipuncture and collected in an 8-ml BD Vacutainer™ CPT™ tube (BD Biosciences, Franklin Lakes, N.J.). Mononuclear cells were isolated according to the manufacturer's instructions and enumerated as previously described for murine macrophages. After resuspension in DMEM with 5% FCS, the cells were plated at the indicated cellular concentrations in 96-well plates and incubated at 37° C. with 10% CO$_2$. After 24 h, the wells were washed with PBS to remove nonadherent cells, and 100 μl of fresh DMEM without fetal calf serum was added to each well. This procedure consistently yields monocyte purities of >80% as assessed by flow cytometry.

Real Time RT-PCR

Total RNA was purified using TRIzol according to the manufacturer's instructions, and gene expression was determined using real time RT-PCR as described by Hartney, J. M., Brown, J., Chu, H. W., Chang, L. Y., Pelanda, R., and Torres, R. M. (2010) Am. J. Pathol 176, 1157-1168. Differences in expression between samples was determined using the comparative threshold cycle ($\Delta\Delta C_T$) as suggested by the manufacturer (Applied Biosystems, Foster City, Calif.), normalizing each sample to either murine or human GAPDH (catalogue numbers 435293E and Hs99999905_m1, respectively). Murine MMP9 (catalogue number Mm00442991_m1), human MMP9 (catalogue number Hs00957562_m1), and human ARHGEF1 (catalogue number Hs00180327_m1) expression was determined using primers and probe sets purchased from Assays on Demand (Applied Biosystems).

MMP9 Quantitation—

MMP9 was quantitated using gelatin zymography as described below for all murine experiments and the human studies displayed in FIGS. 3C, 5B, 13B, 13C, 14C, 15B, 17A, and 17B. For other human studies, we quantitated MMP9 by ELISA in conditioned medium (ELISA TECH, Aurora, Colo.).

Gelatin Zymography—

Novex (Invitrogen) zymogram 10% gelatin gels were used for zymography as indicated per the manufacturer's instructions on conditioned media. Protease activity was detected as a loss of gelatin at the molecular weight of the indicated MMP and quantified by densitometric analysis using ImageJ (National Institutes of Health) software.

Results of the experimental procedures include the following aspects.

Fibronectin-Mediated MMP9 Production by Macrophages is Cell Concentration-Dependent—

Macrophages are induced to express MMP9 when cultured on ECM proteins such as fibronectin. We have reported that the intracellular signaling molecule Arhgef1 functions in macrophages to suppress this protease production in vivo and in vitro and that α5 and β1 integrin signaling is largely required for this in vitro MMP9 production. In the course of that study, we noted a macrophage cell concentration-dependent effect on MMP9 induction. To investigate this in more detail, we cultured thioglycollate-elicited peritoneal macrophages, isolated from wild type or Arhgef1$^{-/-}$ mice, over a range of cell concentrations. The cells were cultured for 48 h on either plastic or fibronectin, and Mmp9 expression was measured. FIG. 10A shows that fibronectin promotes Mmp9 expression by wild type and mutant macrophages over a range of cell concentrations (0.03-0.5×10$^6$ cells/ml) that is maximal at 0.13×10$^6$ cells/ml for both genotypes. As previously reported, in the absence of Arhgef1, fibronectin induction of Mmp9 by macrophages is significantly elevated (FIG. 10A; note they axis is log scale). At the highest cell concentration of 2.0×10$^6$ cells/ml, fibronectin did not appear to induce Mmp9 expression. To determine whether these changes in Mmp9 mRNA were similarly reflected by changes in MMP9 protein, we also measured protease activity in conditioned media. These results show that MMP9 activity is significantly elevated in conditioned media from cells cultured on fibronectin compared with cells cultured on plastic and at all cell concentrations evaluated (FIGS. 10, B and C). Furthermore, Arhgef1-deficient macrophages exhibited significantly higher levels of MMP9 activity compared with wild type cells at 0.25×10$^6$ cells/ml. However, this difference in MMP9 activity between Arhgef1$^{-/-}$ and wild type samples diminishes as cell concentration increases, possibly reflecting a limited linear range when quantitating gelatin zymography.

These results indicate that Mmp9 mRNA expression reflects the status of the macrophages at the time of harvest, whereas MMP9 activity reflects the cumulative production of MMP9 over the culture period. The differences between wild type and Arhgef1-deficient samples are most pronounced at the lower cellular concentrations as analyzed by both qPCR and enzyme activity. Therefore, we used these cell concentrations to investigate how the absence of Arhgef1 alters the expression and production of MMP9 by macrophages cultured on fibronectin.

We initially explored whether the cell concentration dependence could be attributed to cell-to-cell contact. To accomplish this, the cells were fixed after culture on either plastic or fibronectin and stained with crystal violet to determine the extent of cell-to-cell contact. We found minimal cell-to-cell contact between macrophages at cell concentrations that induce MMP9 expression and production (data not shown). At the highest cell concentration (2.0×10$^6$ cells/ml), essentially all macrophages are in contact with adjacent cells, yet MMP9 production remains elevated in the samples cultured on fibronectin (data not shown). Thus, we conclude that cell-to-cell contact does not inhibit MMP9 production at the higher cell concentrations and, conversely, is not required for Mmp9 induction at the lower concentrations. We next considered whether an autocrine/paracrine factor(s) might contribute to macrophage Mmp9 expression.

Thromboxane and PGE$_2$ are Produced by Macrophages Cultured on Fibronectin—

In addition to MMP9 production, ECM proteins have also been shown to promote prostanoid production by myeloid cells. Thus, we questioned whether fibronectin was similarly stimulating production of PGE$_2$ and thromboxane A$_2$ by macrophages in our in vitro cultures. In particular, PGE$_2$ has been reported to function as an autocrine factor for MMP9 production by murine macrophages stimulated with ECM components. We measured PGE$_2$ in our culture supernatant from macrophages incubated on plastic or fibronectin at the cell concentration (0.13×10$^6$ cells/ml) that maximally induced Mmp9 expression. These findings reveal that although conditioned media from macrophages cultured on plastic failed to contain measurable levels of PGE$_2$, conditioned media from macrophages cultured on fibronectin harbor readily detectable levels of this prostaglandin (FIG. 10D).

Thromboxane is another prostanoid produced by peritoneal macrophages when cultured on ECM proteins and was also measured in the supernatant from our macrophage cultures. Similar to PGE$_2$, the thromboxane metabolite TXB$_2$ was also modestly but reproducibly induced by fibronectin in both wild type and mutant macrophages (FIG. 10E). Thus, fibronectin not only induces increased macrophage MMP9 production but also leads to synthesis of the inflammatory prostanoids PGE$_2$ and TXB$_2$. Furthermore, although both prostanoids were elevated in Arhgef1-deficient samples, these increases were not statistically significant, and we conclude that production of these prostanoids does not depend on Arhgef1 expression.

Cyclooxygenase Activity and Thromboxane Receptor Signaling are Required by Macrophages for Fibronectin-Mediated MMP9 Production—

Figure 11:
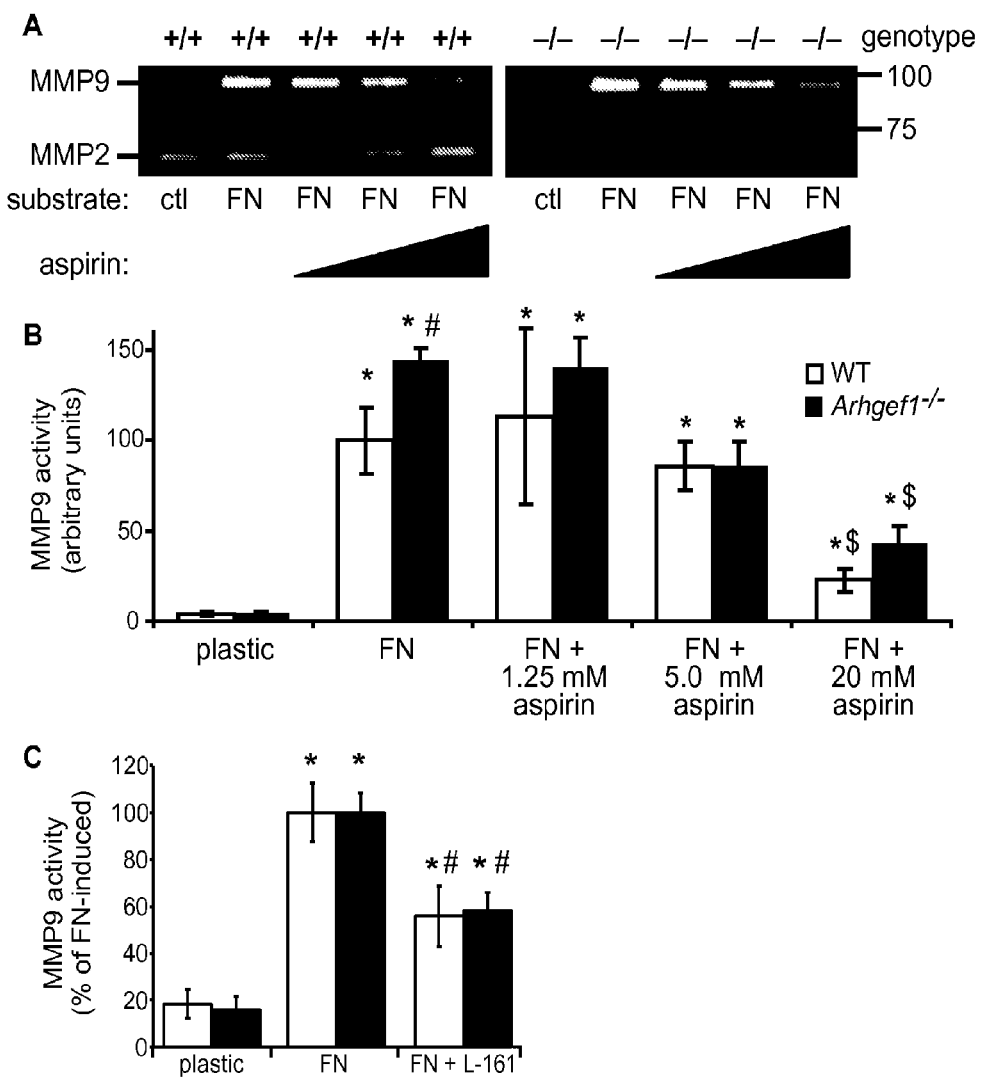
FIG. 11. Cyclooxygenase activity but not EP4 receptor signaling is required for MMP9 production by murine macrophages cultured on fibronectin. A, representative MMP9 gelatin zymograms of conditioned media from peritoneal macrophages cultured on either plastic (ctl) or FN and treated with increasing concentrations of aspirin (1.25, 5.0, and 20 mM, respectively). Wild type (+/+) and Arhgef1$^{-/-}$ (−/−) samples from separate zymograms are shown. Molecular weight standards and respective enzymatic activities of MMP9 and MMP2 are shown. B, quantitation of MMP9 activity as determined by densitometric analysis of zymograms in A. MMP 9 activity is shown in arbitrary units and represents n=6 for both wild type (open bars) and Arhgef1$^{-/-}$ (black bars) samples. The results are compiled from two independent experiments. The data represent the means±S.E. *, $p<0.05$ Student's two-tailed t test compared with conditioned media from cells cultured on plastic. #, $p<0.05$ Student's two-tailed test comparing conditioned media from wild type cells to Arhgef1$^{-/-}$ cells cultured under identical conditions. $, $p<0.05$ Student's two-tailed t test compared with conditioned media from cells cultured on fibronectin. C, quantitation of MMP9 activity in conditioned media from macrophages cultured on fibronectin in the presence of the EP4 antagonist L161,982 (10 µM). MMP9 activity was normalized to fibronectin response for each genotype. The results are compiled from two independent experiments with wild type (open bars, n=5) and Arhgef1$^{-/-}$ (black bars, n=5) samples. The data represent the means±S.E. *, $p<0.05$ Student's two-tailed t test compared with conditioned media from cells cultured on plastic. #, $p<0.05$ Student's two-tailed t test compared with conditioned media from cells cultured on fibronectin.

Prostaglandins and thromboxane are generated from arachidonic acid metabolism by cyclooxygenases; thus we asked whether cyclooxygenase activity was similarly required for fibronectin-mediated induction of MMP9. To address this, we treated macrophages cultured on fibronectin with a cyclooxygenase inhibitor, aspirin, followed by measurement of MMP9 production and activity by gelatin zymography. These data revealed that aspirin inhibited MMP9 activity in a dose-dependent manner in both wild type and Arhgef1-deficient macrophages maximally inhibiting MMP9 activity by 70-75% (FIGS. 11, A and B). We note that the 20 mM maximal concentration of aspirin used is >4-fold above the $IC_{50}$ for COX1 and COX2. Therefore, cyclooxygenase activity is required for optimal fibronectin-induced macrophage MMP9 production, although our results also indicate a minor contribution to MMP9 production via a cyclooxygenase-independent pathway.

We find that fibronectin induces $PGE_2$ production by primary murine macrophages (FIG. 10D), and it has previously been reported that $PGE_2$ signaling via the EP4 receptor is required for production of MMP9 by a murine macrophage cell line after stimulation with a mixture of ECM components. To assess whether a similar dependence on EP4 signaling was also required for fibronectin-induced MMP9 production by primary mouse macrophages, we inhibited EP4 receptor signaling with the EP4 antagonist L-161,982. Treatment of macrophages cultured on fibronectin with 0.4-10 M of the L-161,982 EP4 receptor antagonist maximally suppressed fibronectin-induced MMP9 production by mouse macrophages by only ~40% (FIG. 11 and data not shown) despite completely inhibiting EP4 signaling at these same concentrations. Thus, although EP4 signaling may be necessary for maximal fibronectin-mediated MMP9 production by murine macrophages, there is not an absolute requirement for signaling by this receptor to produce MMP9.

Figure 12:
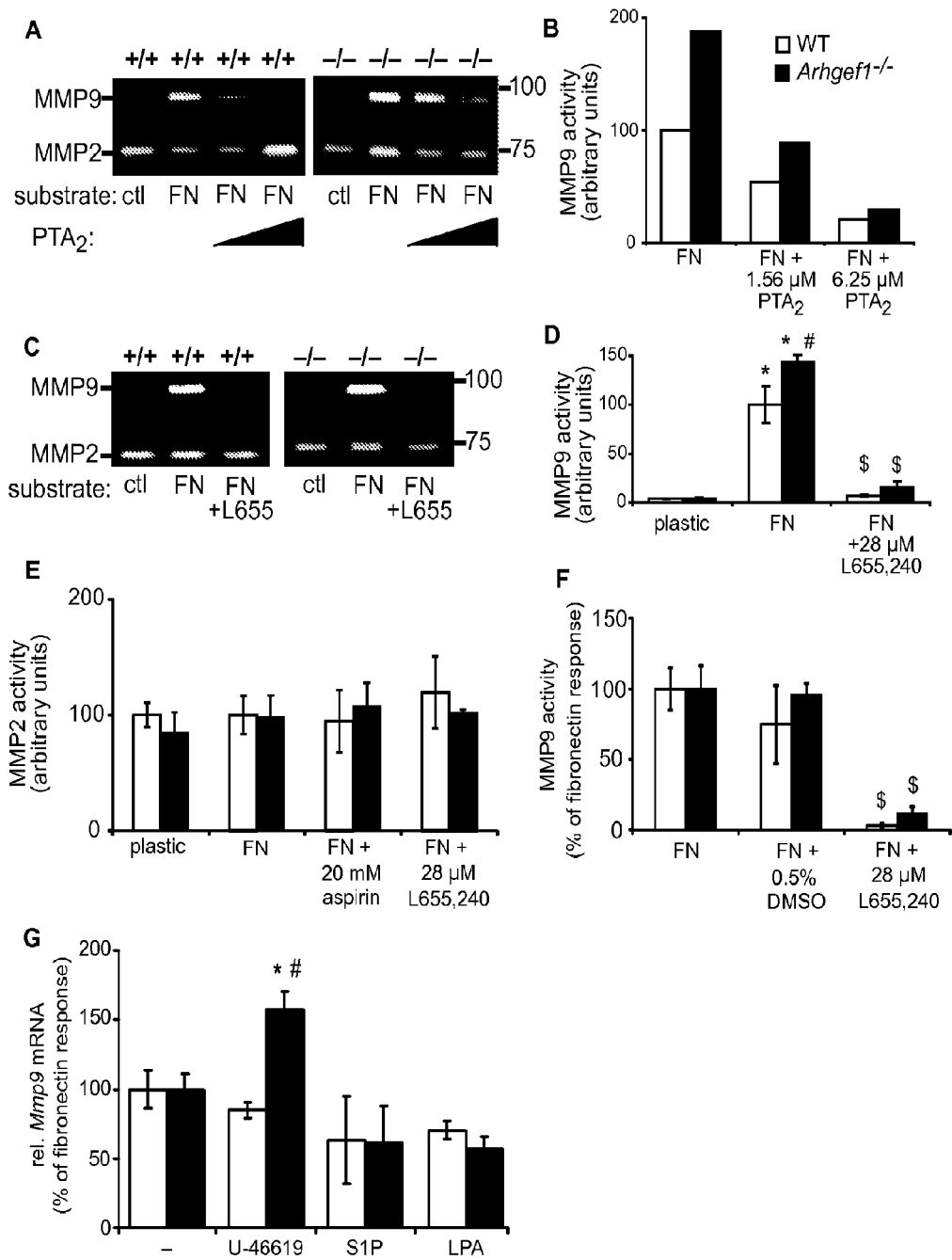
FIG. 12. Thromboxane receptor signaling is necessary for fibronectin-induced MMP9 production by macrophages and is attenuated by Arhgef1. A, representative gelatin zymograms of conditioned media from macrophages cultured on plastic (ctl) or FN and treated with 1.56 or 6.25 µM of the thromboxane receptor antagonist PTA$_2$. Wild type (+/+) and Arhgef1$^{-/-}$ (−/−) samples from separate zymograms are shown. B, quantitation of MMP9 activity as determined by densitometric analysis of zymograms in A. The results are representative of two independent experiments. C, representative zymograms from conditioned media from macrophages cultured on plastic or fibronectin and treated with 28 µM of the thromboxane receptor antagonist L-655,240. D, quantitation of MMP9 activity as determined by densitometric analysis of zymograms in C. The results are compiled from two independent experiments with n=4 for both wild type (open bars) and Arhgef1$^{-/-}$ (black bars) samples. The data represent the means±S.E. *, $p<0.05$ Student's two-tailed t test compared with conditioned media from cells cultured on plastic. #, $p<0.05$ Student's two-tailed t test comparing conditioned media from wild type cells to Arhgef1$^{-/-}$ cells cultured under identical conditions. $, $p<0.05$ Student's two-tailed t test compared with conditioned media from cells cultured on fibronectin. E, MMP2 activity was quantitated in conditioned media as previously described for MMP9. The results are compiled from four independent experiments with n=10 for wild type (open bars) and Arhgef1$^{-/-}$ (black bars) samples cultured on either plastic or fibronectin. For cells treated with 20 mM aspirin, n=6 for wild type (open bars) and Arhgef1$^{-/-}$ (black bars) samples. For cells treated with 28 µM L-655,240, n=4 for wild type (open bars) and Arhgef1$^{-/-}$ (black bars) samples. The data represent the means±S.E. F, MMP9 activity was quantitated as previously described and normalized to a percentage of fibronectin response for each genotype. The cells were either untreated or treated with 0.5% Me$_2$SO or 28 µM L-655,240. The results are compiled from two independent experiments with n=3 for all conditions and genotypes. The data represent the means±S.E. *, $p<0.05$ Student's two-tailed t test compared with conditioned media from cells cultured on fibronectin. G, relative Mmp9 expression was measured by qPCR in macrophages cultured on fibronectin in the presence of the thromboxane receptor agonist (U-46619, 10 nM), S1P (40 nM), or LPA (10 µM). Mmp9 expression is displayed as a percentage of fibronectin response for each genotype. Wild type (open bars, n=12, 6, 3, and 3 for fibronectin, +U-46619, +S1P, and +LPA, respectively) and Arhgef1$^{-/-}$ (black bars, n=14, 6, 3, and 2, respectively) from at least two independent experiments. The data represent the means±S.E. *, $p<0.05$ Student's two-tailed t test compared with conditioned media from cells cultured on fibronectin, #, $p<0.05$ Student's two-tailed t test comparing conditioned media from wild type cells to Arhgef1$^{-/-}$ cells cultured under identical conditions.

Our data thus far show that fibronectin-induced macrophage MMP9 production is largely dependent on cyclooxygenase activity (FIGS. 11, A and B) but less so on EP4 signaling (FIG. 11C). Macrophages also express thromboxane receptors, and because thromboxane is also produced when macrophages are cultured on fibronectin (FIG. 10E), we next assessed whether autocrine thromboxane receptor signaling contributed to MMP9 production and might partially account for the cyclooxygenase dependence. To test this, we inhibited macrophage thromboxane receptor signaling with two different receptor antagonists: $PTA_2$ and L-655, 240. Treatment of mouse macrophages with $PTA_2$ resulted in a reproducible and dose-dependent suppression of MMP9 production and activity reaching 80-85% inhibition in both wild type and Arhgef1-deficient macrophages (FIGS. 12, A and B). Similarly, the L-655,240 thromboxane receptor antagonist also inhibited MMP9 production and activity by ~90% regardless of macrophage genotype (FIGS. 12, C and D). In contrast, MMP2 activity was not affected by either fibronectin stimulation or treatment with 20 mM aspirin or 28 μM L-655,240, indicating that this fibronectin signaling pathway was specific for MMP9 and that neither the cyclooxygenase nor the thromboxane receptor antagonists influenced cell viability (FIG. 12E). Furthermore, because aspirin, L-161,982, pinane-thromboxane $A_2$, and L-655,240 were all dissolved in $Me_2SO$ with a maximal final concentration of <0.5%, we compared the MMP9 activity in samples cultured on fibronectin and treated with 0.5% $Me_2SO$ or 28 μM L-655,240 (FIG. 12F). Although treatment with 28 μM L-655,240 significantly reduced MMP9 activity as previously shown (FIG. 12D), the addition of 0.5% $Me_2SO$ alone did not significantly alter MMP9 activity compared with untreated cells (FIG. 12F).

These findings demonstrate that when thromboxane receptor signaling is prevented, fibronectin-mediated production of MMP9 by mouse macrophages is largely abolished. Considered collectively, thus far these results show that fibronectin induces the production of $PGE_2$, $TXB_2$, and MMP9 by macrophages and Arhgef1 attenuates the production of MMP9. Furthermore, fibronectin-mediated MMP9 production by macrophages appears completely dependent on thromboxane receptor signaling and partially dependent on signaling by the EP4 receptor.

Thromboxane Receptor Signaling is Exaggerated in Arhgef1-Deficient Macrophages—

Prostanoids signal via GPCRs, and Arhgef1 harbors an RGS domain that has been characterized to specifically attenuate signaling by GPCRs that associate with $G\alpha_{12/13}$ heterotrimeric G-protein subunits. Of the nine identified prostanoid receptors, only the thromboxane receptor signals via $G\alpha_{12/13}$, and Arhgef1 has been shown to inhibit thromboxane receptor signaling in leukocytes.

Our results show that fibronectin induces MMP9 production by macrophages in a signaling pathway dependent on thromboxane receptor signaling (FIG. 12, A-D) and that Arhgef1-deficient macrophages display elevated MMP9 production compared with wild type cells (FIG. 10). Therefore, we hypothesized that if Arhgef1 functioned normally to attenuate thromboxane receptor autocrine signaling, then Arhgef1-deficient macrophages would lack this repression and might account for the elevated MMP9 production displayed by Arhgef1$^{-/-}$ macrophages in vitro and in vivo. To directly test this, we pharmacologically manipulated thromboxane receptor signaling in vitro with the thromboxane receptor agonist U-46619. The results from these experiments reveal that although wild type macrophage Mmp9 expression was similar in the presence and absence of U-46619, Arhgef1-deficient macrophages expressed significantly more Mmp9 after U-46619 agonist treatment compared with untreated cells (FIG. 12G).

Besides the thromboxane receptor, macrophages also express $G\alpha_{12/13}$-associated GPCRs specific for the sphingosine1-phosphate (S1P) and lysophosphatidic acid (LPA) lysophospholipids that have been shown to be inhibited by Arhgef1. However, S1P or LPA stimulation of macrophages cultured on fibronectin promoted a slight decrease in Mmp9 expression by both wild type or mutant macrophages (FIG. 12G) consistent with previous reports that these lysophospholipids blunt in vitro macrophage inflammatory responses to LPS stimulation. These results indicate that Arhgef1 attenuation of MMP9 production is specific for thromboxane receptor-mediated signaling. Based on these findings, we conclude that fibronectin induces macrophages to produce MMP9 via thromboxane receptor-dependent autocrine signaling, and Arhgef1 normally functions to attenuate this signaling pathway.

Human Alveolar Macrophages Produce MMP9 and $TXB_2$ in a Cell Concentration-Dependent Manner—

Figure 13:
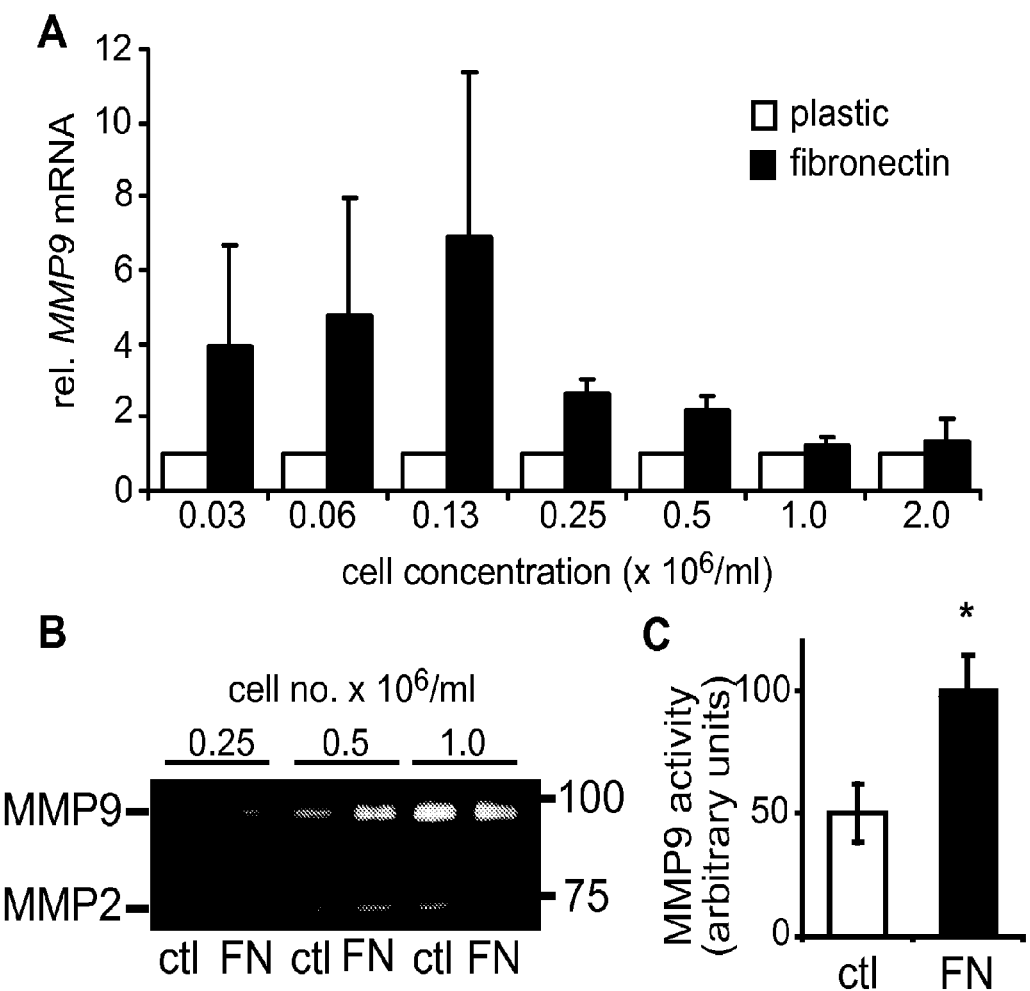
FIG. 13. Human alveolar macrophages are induced to express MMP9 when cultured on fibronectin. A, induction of MMP9 expression by human macrophages cultured on plastic (open bars) or fibronectin (closed bars) as measured by qPCR at the indicated cell concentrations. MMP9 expression on fibronectin is shown as fold over-expression of cells cultured on plastic at each respective concentration from the same individual. The results are compiled from cells obtained from four individuals. The data represent the means±S.E. B, representative gelatin zymogram of conditioned media from human macrophages cultured on either plastic (ctl) or FN at the indicated cell concentrations. C, quantitation of MMP9 activity in conditioned media from cells cultured on FN or plastic (ctl) at 0.125×10$^6$ cells/ml. The results are compiled from cells obtained from six individuals. The data represent the means±S.E. *, $p<0.05$ Student's two-tailed t test compared with cells cultured on plastic.
Figure 14:
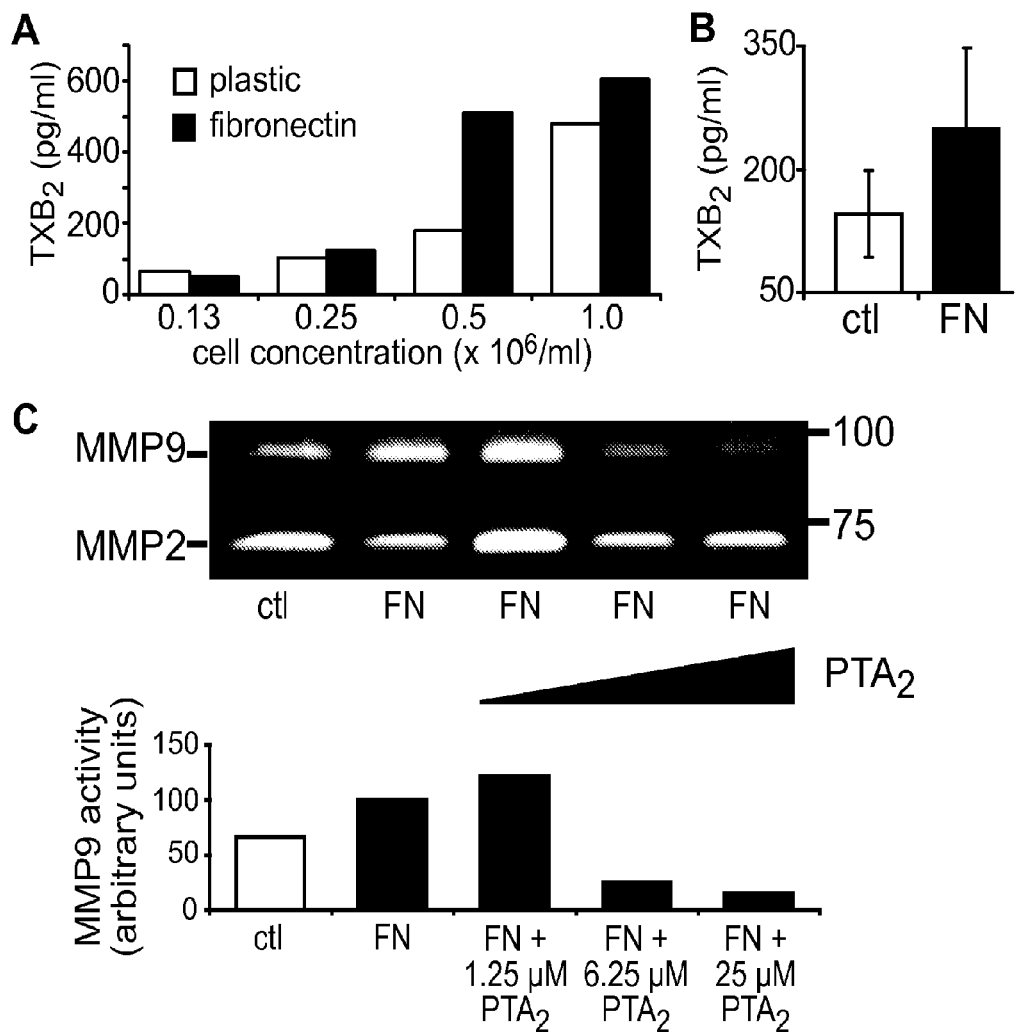
FIG. 14. Human alveolar macrophages produce TXB$_2$ when cultured on fibronectin and thromboxane receptor signaling is required for MMP9 production. A, TXB$_2$ production measured in conditioned media from human macrophages cultured on fibronectin (closed bars) or plastic (open bars) at the indicated cellular concentrations. B, TXB$_2$ measured in conditioned media from macrophages cultured at 0.125×10$^6$ cells/ml on either plastic (ctl) or FN from four individuals. The data represent the means±S.E. C, gelatin zymogram of conditioned media from cells cultured as indicated and in the presence of increasing doses of the thromboxane receptor antagonist PTA$_2$ (at 1.25, 6.25, and 25 µM, respectively). Below the zymogram is quantitation of MMP9 activity by densitometric analysis.

We have observed that Arhgef1-deficient lungs display pathophysiology reminiscent of the lungs from emphysematous individuals. Thus, we were interested to know whether fibronectin-mediated production of MMP9 and prostanoids was also recapitulated with human macrophages. Similar to murine peritoneal macrophages, we observed a strong cell concentration-dependent effect on the induction MMP9 mRNA in human alveolar macrophages cultured on fibronectin with maximal induction when macrophages are plated at $0.13 \times 10^6$ cells/ml (FIG. 13A). Measurement of MMP9 activity in the conditioned media from these cultures by gelatin zymography confirmed an increase in MMP9 production and activity in the samples cultured on fibronectin compared with those cultured on plastic at the same concentration (FIG. 13B). Furthermore, analysis of culture supernatant from macrophages isolated from six individuals confirmed that fibronectin induces human alveolar macrophages to significantly increase the production of active MMP9 (FIG. 13C).

We also determined whether $PGE_2$ and $TXB_2$ were present in the supernatant of human alveolar macrophages cultured on plastic or fibronectin. These results show that although $TXB_2$ was produced by cultured human macrophages in a cell concentration-dependent manner (FIG. 14A), unlike murine macrophages, $PGE_2$ was not produced at measurable levels at any cell concentration and when assessed from macrophages isolated from four different individuals (data not shown). This difference between human and mouse macrophages in the ability to produce $PGE_2$ upon stimulation has been reported. Although human macrophages cultured on fibronectin reproducibly generated more $TXB_2$ compared with that produced when cultured on plastic, we found that this production varied between macrophages isolated from different individuals (FIG. 14B). Importantly, and similar to that observed with murine macrophages, FIG. 14C shows that treatment with the thromboxane receptor antagonist $PTA_2$ resulted in a dose-dependent inhibition (approaching 90%) of MMP9 production. These results demonstrate that thromboxane receptor signaling is also required for fibronectin-induced MMP9 production by human alveolar macrophages. Thus, both human and murine macrophages are induced to express MMP9 and thromboxane when cultured on fibronectin, and MMP9 production is dependent on thromboxane receptor autocrine signaling.

Fibronectin Induces MMP9 and Thromboxane in Peripheral Blood Monocytes and MMP9 Production is Dependent on Thromboxane Receptor Signaling—

Figure 15:
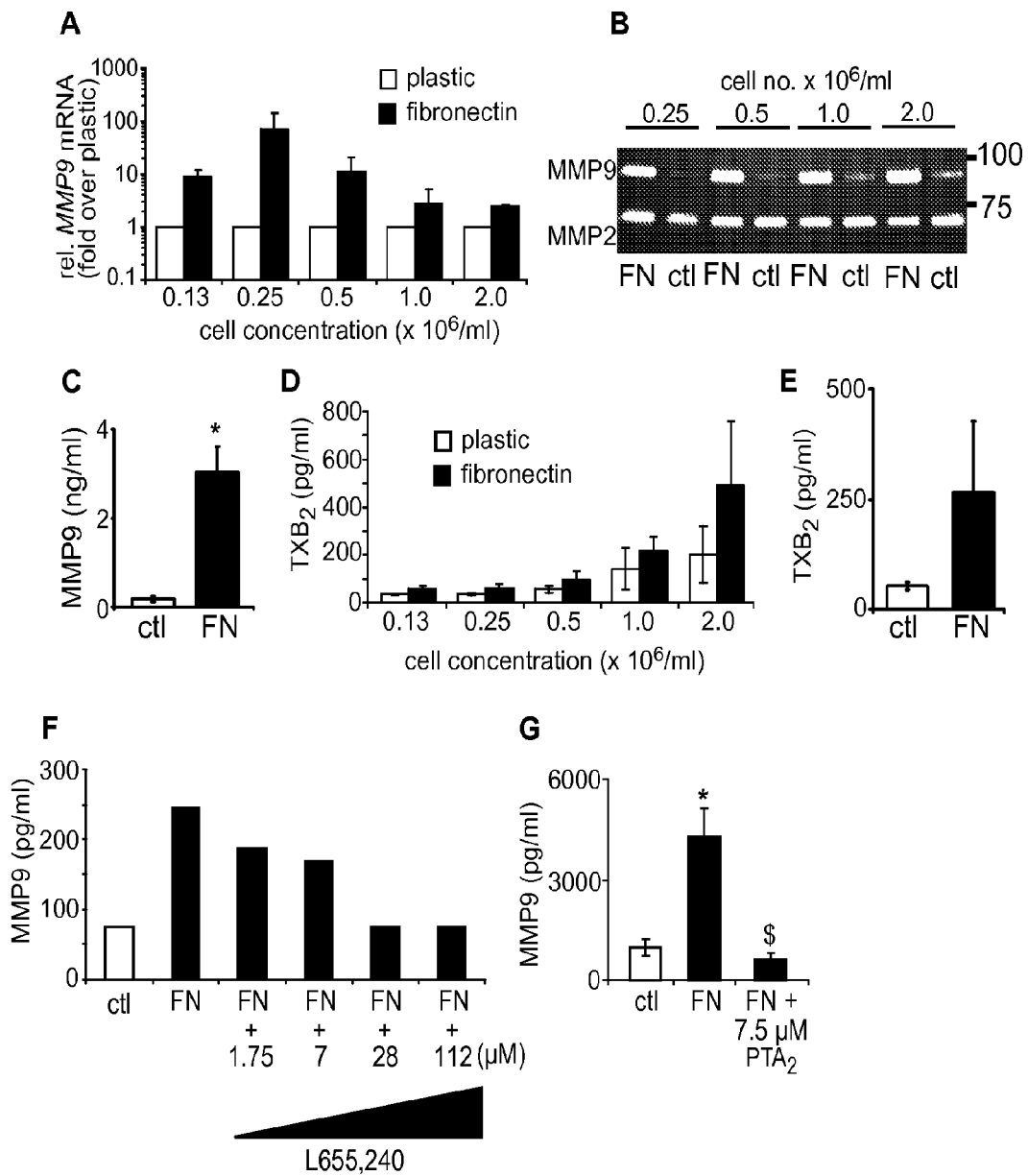
FIG. 15. Human peripheral blood monocytes cultured on fibronectin are induced to express MMP9 and that is dependent on thromboxane receptor signaling. A, MMP9 induction was measured by qPCR at the indicated cell concentrations. MMP9 expression on fibronectin (closed bars) is represented as fold over-expression of cells cultured on plastic at each respective concentration from the same individual. The results are compiled from cells obtained from two individuals. The data represent the means±S.E. B, representative zymogram of conditioned media from monocytes cultured on either plastic (ctl) or FN at the indicated cellular concentrations. C, MMP9 production as measured by ELISA in conditioned media from monocytes cultured on plastic (ctl) or FN at 0.25×10$^6$ cells/ml. The results are compiled from cells obtained from eight individuals. The data represent the means±S.E. D, TXB2 production in conditioned media from monocytes cultured on either plastic or FN at the indicated cellular concentrations. The results are compiled from cells obtained from three individuals. The data represent the means±S.E. E, TXB2 in conditioned media from monocytes cultured on either plastic (ctl) or FN at $0.25 \times 10^6$ cells/ml. The results are compiled from cells obtained from 10 individuals. The data represent the means±S.E. F, MMP9 levels as measured by ELISA in conditioned media from monocytes cultured as indicated with increasing concentrations of the thromboxane receptor antagonist L-655,240 (1.75, 7, 28, and 112 µM). G, MMP9 as measured by ELISA in conditioned media from monocytes cultured as indicated with the thromboxane receptor antagonist $PTA_2$ (7.5 µM). The results are compiled from cells obtained from six individuals. *, $p<0.05$ Student's two-tailed t test compared with conditioned media from cells cultured on plastic. #, $p<0.05$ Student's two-tailed t test compared with conditioned media from cells cultured on fibronectin.

Human peripheral blood monocytes have also been shown to increase MMP9 production when cultured on fibronectin. Therefore, we repeated our in vitro culture with human peripheral blood monocytes and, consistent with both murine peritoneal (FIG. 10A) and human alveolar macrophages (FIG. 13A), a cell concentration-dependent effect was documented for the induction of MMP9 by human monocytes cultured on fibronectin (FIGS. 15, A and B). In experiments with human monocytes, we noted variation in MMP9 activity between cultures established from different individuals. Thus, to alleviate concerns of a limited linear range of activity detected by gelatin zymography, we turned to measuring MMP9 protein by ELISA, and that similarly demonstrated fibronectin was able to induce human monocytes to produce significant amounts of MMP9 over control (FIG. 15C).

As observed with alveolar macrophages, although production of $PGE_2$ was not measurable in the supernatant in multiple subjects over a range of cellular concentrations (data not shown), a cell concentration-dependent increase in $TXB_2$ production by monocytes cultured on fibronectin was observed (FIGS. 15, D and E). Fibronectin-induced MMP9 production by human monocytes was again found to be dependent on thromboxane receptor signaling (FIGS. 3B, 15F, and 15G) as shown by treating cultures with two separate thromboxane receptor antagonists (L-655,240 and $PTA_2$), respectively.

Considering our data collectively, we show that human and murine myeloid cells are stimulated by fibronectin to produce both thromboxane and MMP9, whereas fibronectin-mediated $PGE_2$ production appears restricted to mouse macrophages. Furthermore, the production of MMP9 induced by fibronectin in both human and mouse myeloid cells proceeds by a thromboxane receptor-dependent signaling pathway.

ARHGEF1 Expression is Negatively Correlated with MMP9 Production in Human Monocytes—

Figure 16:
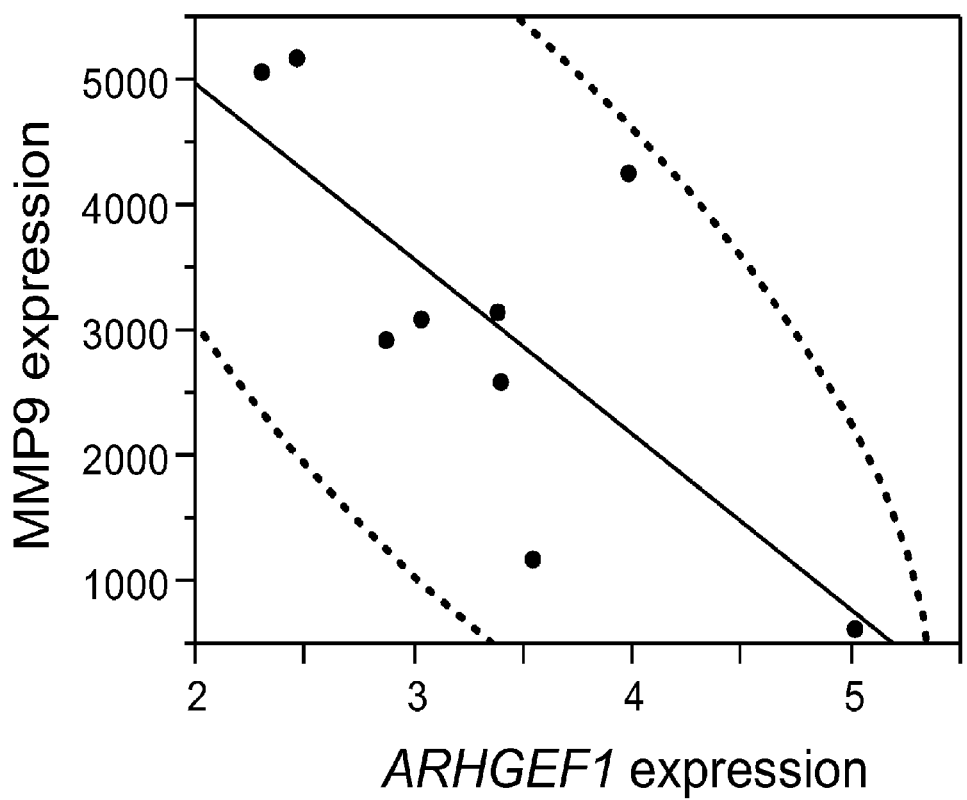
FIG. 16. ARHGEF1 expression negatively correlates with MMP9 production by monocytes cultured on fibronectin. Relative ARHGEF1 expression as measured by RT-PCR is expressed on the x axis. ARHGEF1 expression was normalized to GAPDH expression and displayed relative to the lowest expressing individual. MMP9 production was measured in conditioned media by ELISA and is expressed on they axis. Shown are the results from monocytes obtained from nine individuals cultured under identical conditions where each point represents the values obtained from a separate individual. A Pearson product moment correlation analysis was performed, and a correlation coefficient of −0.737 was obtained with a $p=0.0234$ between ARHGEF1 expression and MMP9 production. The dotted lines denote bivariate normal ellipse for 95% of the values. The solid line represents the linear fit.

As previously noted, although human monocytes are stimulated to produce MMP9 when cultured on fibronectin, a wide range was observed in the amount of MMP9 produced by monocytes from different individuals (e.g. FIGS. 15, C and G). Based on the observation that murine macrophages deficient in Arhgef1 demonstrate exaggerated MMP9 production, we hypothesized that differences in ARHGEF1 expression between individuals may account for some of this variation. To directly test this hypothesis, we compared ARHGEF1 expression with MMP9 production in monocytes and cultured supernatant, respectively, from nine individuals. Specifically, ARHGEF1 expression was measured by qPCR in monocytes, and MMP9 was measured in conditioned media of monocytes cultured on fibronectin. Subsequently, we plotted the relative ARHGEF1 expression in monocytes from a given individual against the amount of MMP9 produced by the same monocytes when cultured on fibronectin (FIG. 16). Consistent with our hypothesis, we found a significant negative correlation between ARHGEF1 expression and MMP9 production in human peripheral blood monocytes (FIG. 16). From these data, we conclude that the level of MMP9 produced by myeloid cell interaction with integrin ligands is at least partially dependent on the level of ARHGEF1 expressed by these leukocytes.

As illustrated by the experiments and analyses described herein, Arhgef1-deficient mice display unprovoked pulmonary pathophysiology resembling a chronic inflammatory disorder, and Arhgef1$^{-/-}$ pulmonary leukocytes, the vast majority which are macrophages, are able to transfer this phenotype to wild type lungs. Possibly contributing to alveolar tissue destruction in Arhgef1$^{-/-}$ lungs, we found that Arhgef1-deficient alveolar macrophages expressed significantly higher levels of several MMPs, including MMP9 that was increased over 100-fold in expression compared with wild type cells. To better understand the signaling pathways that lead to pulmonary pathology in the absence of Arhgef1, we identified an in vitro macrophage culture condition that recapitulated the enhanced MMP9 production by Arhgef1$^{-/-}$ macrophages observed in vivo. Using this system and myeloid cells from both human and mouse, in this study we show that fibronectin-mediated MMP9 production by myeloid cells depends on autocrine thromboxane receptor signaling. Furthermore, Arhgef1 functions normally to attenuate this signaling. Thus, these findings identify a previously unrecognized signaling pathway used by macrophages to produce MMP9 in response to fibronectin.

Adhesion to fibronectin induces Arhgef1-deficient macrophages to produce elevated levels of MMP9 and prostanoids compared with Arhgef1-sufficient wild type cells. Because the RGS activity of Arhgef1 has been characterized to attenuate signaling from GPCRs associated with $G\alpha_{12/13}$ heterotrimeric O-proteins, we sought to identify a putative $G\alpha12/13$-associated GPCR expressed by macrophages that could signal in an autocrine manner and could account for this difference. GPCRs for three different lipids, LPA, S1P, and thromboxane, met this criteria and were expressed by macrophages, and each lipid ligand could feasibly be produced in an autocrine manner. However, when directly tested, the LPA and S1P lysophospholipids modestly repressed MMP9 production, and only thromboxane receptor stimulation led to enhanced MMP9 production by Arhgef1$^{-/-}$ macrophages relative to controls. Together, these results demonstrate that Arhgef1 functions in macrophages to attenuate thromboxane receptor signaling and that when Arhgef1-deficient macrophages are stimulated with fibronectin, exaggerated thromboxane receptor signaling leads to elevated MMP9 production.

One conclusion from our results is that fibronectin-stimulated production of MMP9 by both human and mouse macrophages is dependent on thromboxane receptor signaling (FIGS. 4, 5, 12, 14, 15 and 17) and less dependent on cyclooxygenase activity (FIGS. 5, 11, and data not shown). Cyclooxygenase activity also is required for the production of $PGE_2$, and contrary to our findings, it was previously suggested that $PGE_2$-EP4 autocrine signaling was necessary for MMP9 production by mouse macrophages. The basis for the apparent difference with our findings is not clear but may reflect our measurement of MMP9 activity produced by primary macrophages after culture on fibronectin versus the stimulation of the RAW246.7 macrophage cell line with ECM components derived from vascular smooth muscle cells and measuring MMP9 by Western blot analysis. Perhaps more importantly, although we reproducibly measured elevated levels of $PGF_2$ in the supernatant of fibronectin-stimulated mouse macrophages, we were unable to detect $PGE_2$ in the supernatants of similarly stimulated human macrophages or monocytes that were isolated from multiple individuals and over a range of cellular concentrations. In contrast, thromboxane production was always induced and detected after fibronectin stimulation of both murine and human macrophages. Together, these data suggest differences in prostanoid metabolism between integrin-stimulated murine and human macrophages with regards to $PGE_2$ production. These data are supported by a recent investigation using mass spectrometry to identify prostanoids from toll-like receptor-stimulated human and murine macrophages. In that study, stimulated murine macrophages were found to produce $PGE_2$, whereas stimulated human macrophages only produced thromboxane and did not produce detectable levels of $PGE_2$. Despite these interspecies differences in $PGE_2$ production, fibronectin induces both human and murine macrophages to produce thromboxane and MMP9 and supports our identification that thromboxane receptor signaling is required for the fibronectin induction of MMP9 by both human and mouse myeloid cells.

Human and murine macrophages have long been known to produce thromboxane in response to zymosan and a number of other stimuli including LPS, platelet-activating factor, complement components, and CD44 ligation. Myeloid cells also express thromboxane receptors, and thromboxane autocrine or paracrine signaling by human monocytes has been shown to participate in the production of the TNFα and IL-1β pro-inflammatory cytokines. Our data show that macrophage autocrine thromboxane receptor signaling is also required for MMP9 production after adhesion to fibronectin. MMP9 is another pro-inflammatory mediator produced by macrophages during the inflammatory response where it acts on chemokines and extracellular matrix proteins to regulate the recruitment of inflammatory cells and tissue remodeling. Thus, an autocrine thromboxane receptor signaling pathway appears to contribute to macrophage production of pro-inflammatory mediators during inflammation. Whether this pathway is used physiologically by macrophages to generally promote inflammation remains to be established. However, the chronic pulmonary inflammatory environment promoted by Arhgef1-deficient leukocytes, which cannot repress thromboxane receptor signaling, would support this notion. Indeed, inhibiting thromboxane synthesis or receptor signaling attenuates both in vitro macrophage production of the TNF-α and IL-1β pro-inflammatory cytokines and in viva features of inflammation.

Our results identify a common human and murine macrophage thromboxane receptor signaling pathway induced by fibronectin and, in mouse cells, attenuated by Arhgef1. However, as opposed to results obtained with genetically identical wild type and Arhgef1$^{-/-}$ macrophages, we found variation in fibronectin-induced MMP9 production by human macrophages and monocytes. Thus, we considered whether this variation reflected differences in ARHGEF1 expression by myeloid cells from different individuals and found a >2.5-fold variation in monocyte ARHGEF1 expression from nine individuals. Importantly, a significant inverse correlation was shown between ARHGEF1 expression and in vitro fibronectin-induced MMP9 production. Thus, as with mouse macrophages, ARHGEF1 also appears to function in human myeloid cells to attenuate thromboxane receptor signaling.

Although macrophages play an instrumental role in the initiation, maintenance, and resolution of inflammation, they are also associated with the pathogenesis of many diseases associated with chronic inflammatory disorders such as chronic obstructive pulmonary disease, atherosclerosis, and cancer. The data presented in this study not only identify a novel macrophage signaling pathway that may contribute to chronic inflammatory processes that drive these diseases but also reveal therapeutic points for intervention.

Various thromboxane receptor antagonists can be useful in treatment methods based on the present technology. Thromboxane receptor antagonists include the following compounds, with suppliers indicated in brackets and common synonyms listed in parentheses: pinane thromboxane A2 (also known as PTXA2; $PTA_2$; and (18-(1alpha,2beta(Z),3alpha(1E,3S*),5alpha))-7-(3-(3-Hydroxy-1-octenyl)-6,6-dimethylbicyclo(3.1.1)hept-2-yl)-5-heptenoic acid); L-655,240 (also known as 1-[(4-Chlorophenyl)methyl]-5-fluoro-α,α,3-trimethyl-1H-indole-2-propanoic acid); L-670,596 (also known as (−)-6-8-Difluoro-2,3,4,9-tetrahydro-9-[[4-(methylsulfonyl)phenyl]methyl]-1H-carbazole-1-acetic acid); Terutroban [Servier Laboratories] (also known as S-18886; Terutroban salts, including sodium; and 3-[6-[(4-chlorophenyl)sulfonylamino]-2-methyl-5,6,7,8-tetrahydronaphthalen-1-yl]propanoate); PRT061103 [Portola Pharmaceuticals]; Ifetroban [Cumberland Pharmaceuticals] (also known as 3-[2-({(1s,2r,3s)-3-[4-(pentylcarbamoyl)-1,3-oxazol-2-yl]-7-oxabicyclo[2.2.1]hept-2-yl}methyl)phenyl] propanoic acid); Ramatroban [Bayer AG] (also known as BAY-u-3405; 3-[(3R)-3-[(4-fluorophenyl)sulfonylamino]-1,2,3,4-tetrahydrocarbazol-9-yl]propanoic acid; and (3R)-3-[[(4-Fluorophenyl)sulfonyl]amino]-1,2,3,4-tetrahydro-9H-carbazole-9-propanoic acid); Seratrodast [Abbott; TAP Pharmaceuticals; Takeda Chemical Industries] (also known as AA-2414; 7-phenyl-7-(2,4,5-trimethyl-3,6-dioxocyclohexa-1,4-dien-1-yl)heptanoic acid; and 7-(3,5,6-Trimethyl-1,4-benzoquinon-2-yl)-7-phenylheptanoic acid); Z-335 [Zeria Pharmaceutical Co., Japan] (also known as Z-335 salts, including sodium; and 2-[2-[[(4-chlorophenyl)sulfonylamino]methyl]-2,3-dihydro-1H-inden-5-yl]acetate); Ridogrel [Janssen Pharmaceuticals] (also known as 5-[(E)-[pyridin-3-yl-[3-(trifluoromethyl)phenyl]methylidene] amino]oxypentanoic acid); Terbogrel [Boehringer Ingelheim] (also known as (E)-6-[3-[(N-tert-butyl-N-cyanocarbamimidoyl)amino]phenyl]-6-pyridin-3-ylhex-5-enoic acid); ICI-185,282 [AstaZeneca] (also known as 5-(Z)-7-(4-o-Hydroxyphenyl-2-trifluoromethyl-1,3 dioxan-cis-5-yl)heptenoic acid); and ICI-192,605 (also known as 4-(Z)-6-(2-o-Chlorophenyl-4-o-hydroxyphenyl-1,3-dioxan-cis-5-yl)hexenoic acid); among others. Various salt, acid, and free base forms of such thromboxane receptor antagonists can be used, including various combinations thereof.

The thromboxane receptor antagonist can be administered to a subject in a therapeutically effective amount, which is sufficient to abrogate, substantially inhibit, slow or reverse the progression of a pulmonary disease condition associated with thromboxane receptor activity, to substantially ameliorate clinical symptoms of a such a condition, or to substantially prevent, delay, or reduce the appearance of clinical symptoms of such a condition. The inhibitory amount may be determined directly by measuring the inhibition of thromboxane receptor activity, or, for example, where the desired effect is an effect on an activity downstream of thromboxane receptor activity in a pathway that includes the thromboxane receptor, the inhibition may be measured by measuring a downstream effect, such as measuring MMP9 production, as demonstrated herein.

The amount of the thromboxane receptor antagonist compound that constitutes a therapeutically effective amount can vary depending on such parameters as the compound and its potency, the half-life of the compound in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the compound or that will have an effect on thromboxane receptor activity, or a pathway mediated by thromboxane receptor activity. The therapeutically effective amount can fall in a relatively broad range and can be determined through routine trials. Likewise, the thromboxane receptor antagonist can be administered by one or more parenteral and enteral administration routes. Particular examples of administration routes include oral, intravenous, intraperitoneal, and inhalation by aerosolization.

Figure 17:
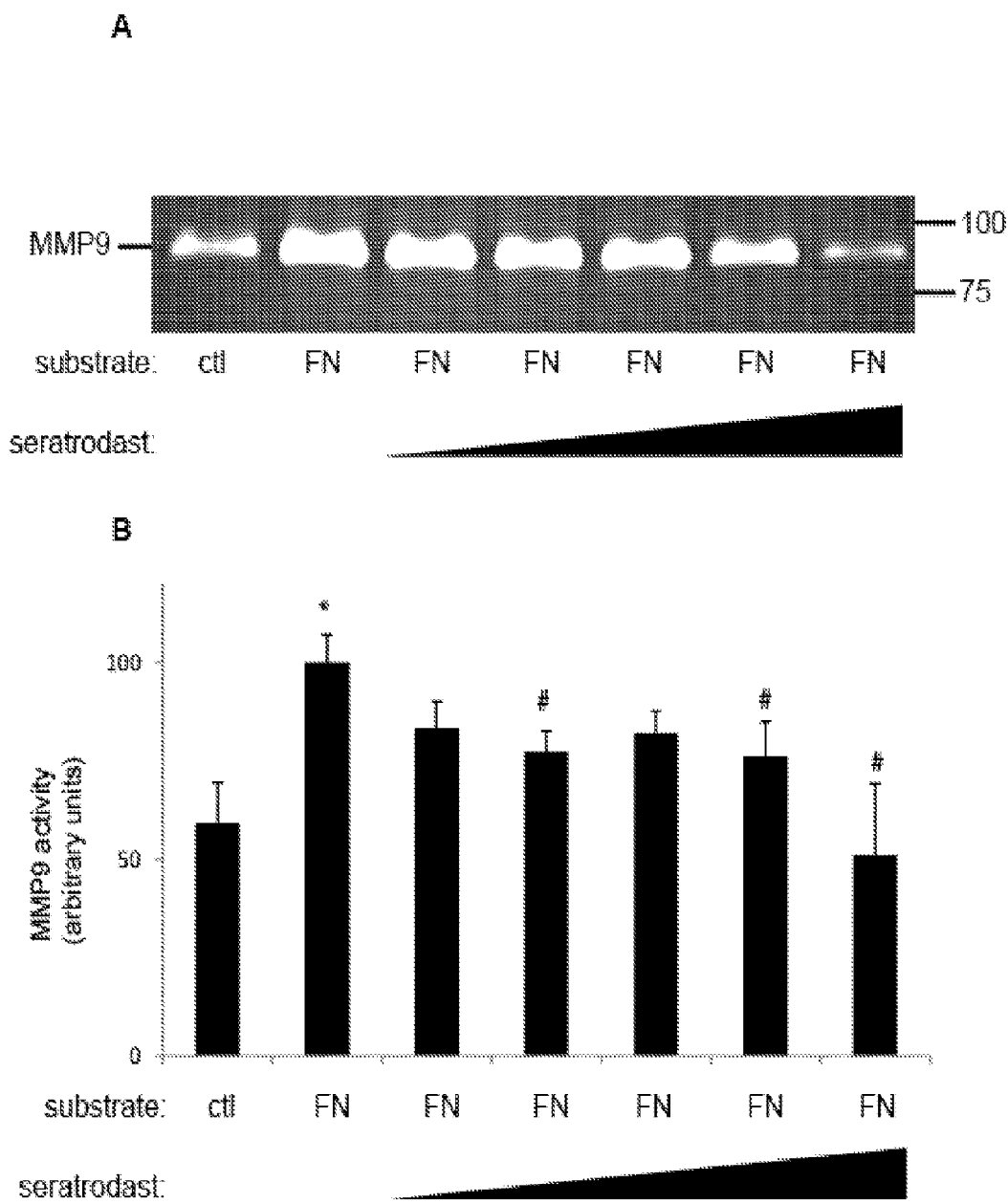
FIG. 17. Seratrodast (AA-2414) treatment on peripheral blood monocytes from 3 COPD patients. Generated dose response curve going firm 0.4 µM to 260 µM. Measured response by gelatin zymography of conditioned media. A is a representative zymogram from a single individual COPD patient. B depicts results compiled from three COPD patients. *, $p<0.05$ for ctl vs FN; #, $p<0.05$ FN vs FN+seratrodast.
Figure 18:
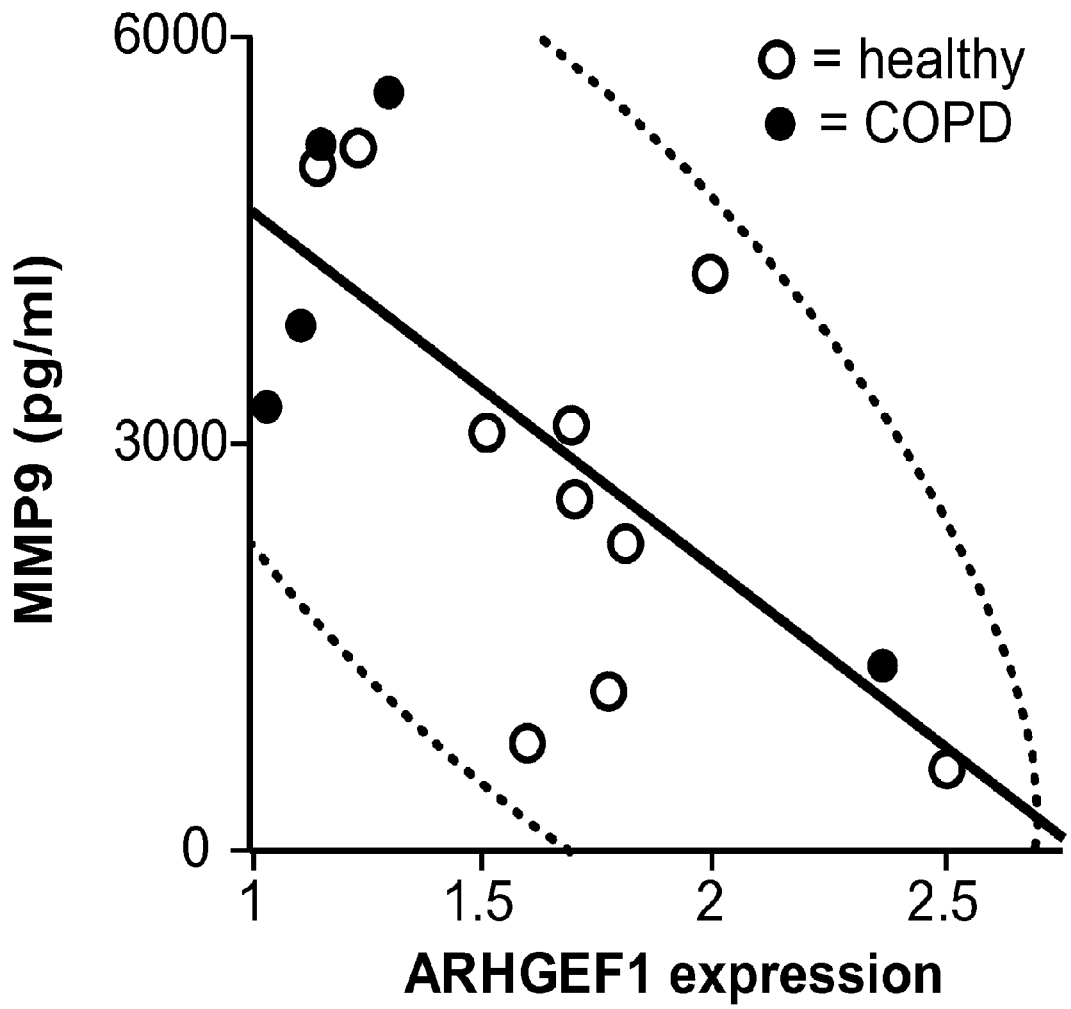
FIG. 18. Human PB healthy and COPD subject correlation. Shown are the results from monocytes obtained from healthy subjects (open circles, n=9) and patients with COPD (solid circles, n=5) cultured on FN under identical conditions. Relative ARHGEF1 expression is expressed on the X-axis. MMP9 production in conditioned media is expressed on the Y-axis. A Pearson-product moment correlation analysis was performed and a correlation coefficient of −0.705 with a $P=0.0016$ between ARHGEF1 expression and MMP9 production. Dotted line denotes bivariate normal ellipse for 95% of the values. Solid line represents the linear fit.

As another example, the thromboxane receptor antagonist seratrodast (AA-2414) was used on peripheral blood monocytes from 3 COPD patients and data collected as shown in FIG. 17. A dose response curve ranging from 0.4 µM to 260 µM of seratrodast was generated which shows an inverse relationship between MMP9 activity and seratrodast dose. Likewise, zymograms of conditioned media illustrating MMP9 activity were performed further demonstrating the inverse relationship between MMP9 activity and seratrodast dose.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of treating chronic obstructive pulmonary disease in a subject comprising administering to the subject a therapeutically effective amount of a thromboxane receptor antagonist, wherein an expression of Arhgef1 in an alveolar macrophage, a monocyte, a monocyte-derived macrophage, or a neutrophil from the subject is reduced compared to an expression of Arhgef1 in an alveolar macrophage, a monocyte, a monocyte-derived macrophage, or a neutrophil from a subject without chronic obstructive pulmonary disease.

2. A method of treating a subject having chronic obstructive pulmonary disease comprising:
   administering a therapeutically effective amount of a thromboxane receptor antagonist to the subject having the pulmonary disease;
   wherein the subject is identified as having the pulmonary disease by:
      determining leukocyte expression of Arhgef1 in the subject, wherein the leukocyte comprises an alveolar macrophage, a monocyte, a monocyte-derived macrophage, or a neutrophil; and
      identifying the subject as having the pulmonary disease when the leukocyte expression of Arhgef1 in the subject is reduced compared to leukocyte expression of Arhgef1 in a subject without chronic obstructive pulmonary disease.

3. A method of selecting a candidate compound for treating chronic obstructive pulmonary disease in a subject comprising:
   exposing a leukocyte comprising a thromboxane receptor to a compound, wherein the leukocyte has a reduced expression of Arhgef1 compared to an expression of Arhgef1 in a leukocyte from a subject without chronic obstructive pulmonary disease;
   determining if the compound inhibits the thromboxane receptor; and
   selecting the compound as a candidate compound for treating the pulmonary disease when the compound inhibits the thromboxane receptor.

4. The method of claim 3, wherein the leukocyte comprises an alveolar macrophage, a monocyte, a monocyte-derived macrophage, or a neutrophil.

5. A method of treating a subject having chronic obstructive pulmonary disease comprising:
   exposing a leukocyte comprising a thromboxane receptor to a compound, wherein the leukocyte has a reduced expression of Arhgef1 compared to an expression of Arhgef1 in a leukocyte from a subject without chronic obstructive pulmonary disease;
   determining if the compound inhibits the thromboxane receptor;
   selecting the compound as a candidate compound when the compound inhibits the thromboxane receptor; and
   administering a therapeutically effective amount of the candidate compound to the subject having chronic obstructive pulmonary disease.

* * * * *